(12) United States Patent
Leppänen et al.

(10) Patent No.: US 10,471,305 B2
(45) Date of Patent: Nov. 12, 2019

(54) MODIFICATION OF AN EXERCISE PLAN

(71) Applicant: Nokia Technologies Oy, Espoo (FI)

(72) Inventors: Jussi Leppänen, Tampere (FI); Miikka Vilermo, Siuro (FI); Antti Eronen, Tampere (FI); Arto Lehtiniemi, Lempäälä (FI)

(73) Assignee: Nokia Technologies Oy, Espoo (FI)

( * ) Notice: Subject to any disclaimer, the term of this patent is extended or adjusted under 35 U.S.C. 154(b) by 552 days.

(21) Appl. No.: 14/873,496

(22) Filed: Oct. 2, 2015

(65) Prior Publication Data

US 2016/0096075 A1 Apr. 7, 2016

(30) Foreign Application Priority Data

Oct. 7, 2014 (EP) .................................... 14187922

(51) Int. Cl.
*A63B 24/00* (2006.01)

(52) U.S. Cl.
CPC ................ *A63B 24/0075* (2013.01)

(58) Field of Classification Search
CPC .................. A63B 24/0075; G06F 19/3481
USPC ........................................... 434/247
See application file for complete search history.

(56) References Cited

U.S. PATENT DOCUMENTS

| 2008/0009275 A1 | 1/2008 | Werner et al. |
| 2012/0015778 A1* | 1/2012 | Lee ..................... A63B 71/0622 482/8 |
| 2013/0141421 A1 | 6/2013 | Mount et al. ................. 345/419 |

FOREIGN PATENT DOCUMENTS

| EP | 2407219 A2 | 1/2012 |
| EP | 2657865 A1 | 10/2013 |
| WO | 2006065679 A2 | 6/2006 |

OTHER PUBLICATIONS

European Search Report and Written Opinion received for corresponding Patent Application No. 14187922.1, dated Mar. 23, 2015, 6 pages.

* cited by examiner

*Primary Examiner* — Paul A D'Agostino
(74) *Attorney, Agent, or Firm* — Harrington & Smith

(57) ABSTRACT

A method comprising determining an exercise plan for a user of an apparatus, entering a collaborative exercise session with a separate apparatus, determining a portion of the exercise plan that corresponds with a location of the user, causing display of an exercise indicator that indicates exercise instruction information that corresponds with the portion of the exercise plan, receiving exercise information from the separate apparatus based, at least in part, on the collaborative exercise session, modifying the exercise plan to generate a modified exercise plan based, at least in part, on the exercise information received from the separate apparatus, determining a portion of the modified exercise plan that corresponds with the location of the user, and causing display of another exercise indicator that indicates exercise instruction information that corresponds with the portion of the modified exercise plan is disclosed.

16 Claims, 19 Drawing Sheets

| | | |
|---|---|---|
| 602 | Exercise Route Segment | Exercise Instruction Information | 612
| 604 | Exercise Route Segment | Exercise Instruction Information | 614
| 606 | Exercise Route Segment | Exercise Instruction Information | 616

FIG. 6A

| | | |
|---|---|---|
| 622 | Exercise Route Segment | Exercise Pace | 632
| 624 | Exercise Route Segment | Exercise Pace | 634
| 626 | Exercise Route Segment | Exercise Pace | 636

FIG. 6B

| | | |
|---|---|---|
| 642 | Exercise Route Segment | Physiological State | 652
| 644 | Exercise Route Segment | Physiological State | 654
| 646 | Exercise Route Segment | Physiological State | 656

FIG. 6C

| Exercise Route Segment 662 | Exercise Activity 672 | Exercise Pace 682 | Physiological State 692 |
|---|---|---|---|
| Exercise Route Segment 664 | Exercise Activity 674 | Exercise Pace 684 | Physiological State 694 |
| Exercise Route Segment 666 | Exercise Activity 676 | Exercise Pace 686 | Physiological State 696 |

FIG. 6D

MODIFICATION OF AN EXERCISE PLAN

TECHNICAL FIELD

The present application relates generally to modification of an exercise plan.

BACKGROUND

In recent times, electronic apparatuses have become increasingly pervasive in our society. In many circumstances, a user may often interact with other electronic apparatuses and/or electronic apparatus peripherals in performance of various activities, in various contexts, and/or the like. As such, it may be desirable to configure an apparatus such that a user of the apparatus may interact with the other electronic apparatuses and/or electronic apparatus peripherals in a manner that avoids confusion and delay.

SUMMARY

Various aspects of examples of the invention are set out in the claims.

One or more embodiments may provide an apparatus, a computer readable medium, a non-transitory computer readable medium, a computer program product, and/or a method for determining an exercise plan for a user of an apparatus, entering a collaborative exercise session with a separate apparatus, determining a portion of the exercise plan that corresponds with a location of the user, causing display of an exercise indicator that indicates exercise instruction information that corresponds with the portion of the exercise plan, receiving exercise information from the separate apparatus based, at least in part, on the collaborative exercise session, modifying the exercise plan to generate a modified exercise plan based, at least in part, on the exercise information received from the separate apparatus, determining a portion of the modified exercise plan that corresponds with the location of the user, and causing display of another exercise indicator that indicates exercise instruction information that corresponds with the portion of the modified exercise plan.

One or more embodiments may provide an apparatus, a computer readable medium, a computer program product, and/or a non-transitory computer readable medium having means for determining an exercise plan for a user of an apparatus, the exercise plan correlating exercise instruction information with location information, means for entering a collaborative exercise session with a separate apparatus, means for determining a portion of the exercise plan that corresponds with a location of the user, the exercise plan correlating exercise instruction information with location information, means for causing display of an exercise indicator that indicates exercise instruction information that corresponds with the portion of the exercise plan, means for receiving exercise information from the separate apparatus based, at least in part, on the collaborative exercise session, means for modifying the exercise plan to generate a modified exercise plan based, at least in part, on the exercise information received from the separate apparatus, means for determining a portion of the modified exercise plan that corresponds with the location of the user, and means for causing display of another exercise indicator that indicates exercise instruction information that corresponds with the portion of the modified exercise plan.

An apparatus comprising at least one processor and at least one memory, the memory comprising machine-readable instructions, that when executed cause the apparatus to perform determination of an exercise plan for a user of the apparatus, the exercise plan correlating exercise instruction information with location information, entering of a collaborative exercise session with a separate apparatus, determination of a portion of the exercise plan that corresponds with a location of the user, causation of display of an exercise indicator that indicates exercise instruction information that corresponds with the portion of the exercise plan, receipt of exercise information from the separate apparatus based, at least in part, on the collaborative exercise session, modification of the exercise plan to generate a modified exercise plan based, at least in part, on the exercise information received from the separate apparatus, determination of a portion of the modified exercise plan that corresponds with the location of the user, and causation of display of another exercise indicator that indicates exercise instruction information that corresponds with the portion of the modified exercise plan.

BRIEF DESCRIPTION OF THE DRAWINGS

For a more complete understanding of embodiments of the invention, reference is now made to the following descriptions taken in connection with the accompanying drawings in which:

FIGS. 6A-6D are diagrams illustrating an exercise plan according to at least one example embodiment;

DETAILED DESCRIPTION OF THE DRAWINGS

Figure 1:
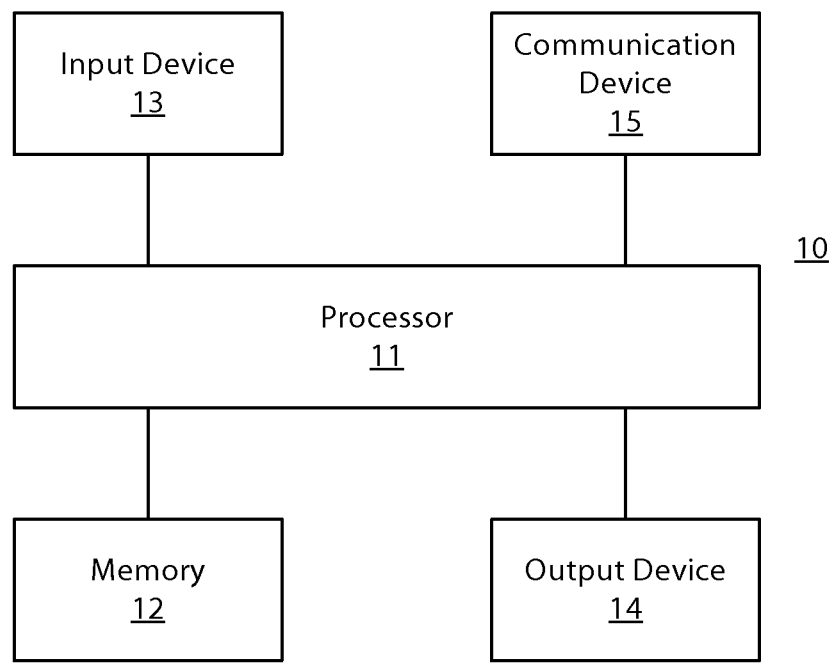
FIG. 1 is a block diagram showing an apparatus according to at least one example embodiment.

An embodiment of the invention and its potential advantages are understood by referring to FIGS. 1 through 18 of the drawings.

Some embodiments will now be described more fully hereinafter with reference to the accompanying drawings, in which some, but not all, embodiments are shown. Various embodiments of the invention may be embodied in many different forms and should not be construed as limited to the embodiments set forth herein; rather, these embodiments are provided so that this disclosure will satisfy applicable legal requirements. Like reference numerals refer to like elements throughout. As used herein, the terms "data," "content," "information," and similar terms may be used interchangeably to refer to data capable of being transmitted, received and/or stored in accordance with embodiments of the present invention. Thus, use of any such terms should not be taken to limit the spirit and scope of embodiments of the present invention.

Additionally, as used herein, the term 'circuitry' refers to (a) hardware-only circuit implementations (e.g., implementations in analog circuitry and/or digital circuitry); (b) combinations of circuits and computer program product(s) comprising software and/or firmware instructions stored on one or more computer readable memories that work together to cause an apparatus to perform one or more functions described herein; and (c) circuits, such as, for example, a microprocessor(s) or a portion of a microprocessor(s), that require software or firmware for operation even if the software or firmware is not physically present. This definition of 'circuitry' applies to all uses of this term herein, including in any claims. As a further example, as used herein, the term 'circuitry' also includes an implementation comprising one or more processors and/or portion(s) thereof and accompanying software and/or firmware. As another example, the term 'circuitry' as used herein also includes, for example, a baseband integrated circuit or applications processor integrated circuit for a mobile phone or a similar integrated circuit in a server, a cellular network apparatus, other network apparatus, and/or other computing apparatus.

As defined herein, a "non-transitory computer-readable medium," which refers to a physical medium (e.g., volatile or non-volatile memory device), can be differentiated from a "transitory computer-readable medium," which refers to an electromagnetic signal.

FIG. 1 is a block diagram showing an apparatus, such as an electronic apparatus 10, according to at least one example embodiment. It should be understood, however, that an electronic apparatus as illustrated and hereinafter described is merely illustrative of an electronic apparatus that could benefit from embodiments of the invention and, therefore, should not be taken to limit the scope of the invention. While electronic apparatus 10 is illustrated and will be hereinafter described for purposes of example, other types of electronic apparatuses may readily employ embodiments of the invention. Electronic apparatus 10 may be a personal digital assistant (PDAs), a pager, a mobile computer, a desktop computer, a television, a gaming apparatus, a laptop computer, a tablet computer, a media player, a camera, a video recorder, a mobile phone, a global positioning system (GPS) apparatus, a wearable apparatus, a head mounted apparatus, a projector, a near eye display, and/or any other types of electronic systems. Moreover, the apparatus of at least one example embodiment need not be the entire electronic apparatus, but may be a component or group of components of the electronic apparatus in other example embodiments. For example, the apparatus may be an integrated circuit, a set of integrated circuits, and/or the like.

Furthermore, apparatuses may readily employ embodiments of the invention regardless of their intent to provide mobility. In this regard, even though embodiments of the invention may be described in conjunction with mobile applications, it should be understood that embodiments of the invention may be utilized in conjunction with a variety of other applications, both in the mobile communications industries and outside of the mobile communications industries. For example, the apparatus may be, at least part of, a non-carryable apparatus, such as a large screen television, an electronic table, a kiosk, an automobile, and/or the like.

In at least one example embodiment, electronic apparatus 10 comprises processor 11 and memory 12. Processor 11 may be any type of processor, controller, embedded controller, processor core, and/or the like. In at least one example embodiment, processor 11 utilizes computer program code to cause an apparatus to perform one or more actions. Memory 12 may comprise volatile memory, such as volatile Random Access Memory (RAM) including a cache area for the temporary storage of data and/or other memory, for example, non-volatile memory, which may be embedded and/or may be removable. The non-volatile memory may comprise an EEPROM, flash memory and/or the like. Memory 12 may store any of a number of pieces of information, and data. The information and data may be used by the electronic apparatus 10 to implement one or more functions of the electronic apparatus 10, such as the functions described herein. In at least one example embodiment, memory 12 includes computer program code such that the memory and the computer program code are configured to, working with the processor, cause the apparatus to perform one or more actions described herein.

The electronic apparatus 10 may further comprise a communication device 15. In at least one example embodiment, communication device 15 comprises an antenna, (or multiple antennae), a wired connector, and/or the like in operable communication with a transmitter and/or a receiver. In at least one example embodiment, processor 11 provides signals to a transmitter and/or receives signals from a receiver. The signals may comprise signaling information in accordance with a communications interface standard, user speech, received data, user generated data, and/or the like. Communication device 15 may operate with one or more air interface standards, communication protocols, modulation types, and access types. By way of illustration, the electronic communication device 15 may operate in accordance with second-generation (2G) wireless communication protocols IS-136 (time division multiple access (TDMA)), Global System for Mobile communications (GSM), and IS-95 (code division multiple access (CDMA)), with third-generation (3G) wireless communication protocols, such as Universal Mobile Telecommunications System (UMTS), CDMA2000, wideband CDMA (WCDMA) and time division-synchronous CDMA (TD-SCDMA), and/or with fourth-generation (4G) wireless communication protocols, wireless networking protocols, such as 802.11, short-range wireless protocols, such as Bluetooth, and/or the like. Communication device 15 may operate in accordance with wireline protocols, such as Ethernet, digital subscriber line (DSL), asynchronous transfer mode (ATM), and/or the like.

Processor 11 may comprise means, such as circuitry, for implementing audio, video, communication, navigation, logic functions, and/or the like, as well as for implementing embodiments of the invention including, for example, one or more of the functions described herein. For example, processor 11 may comprise means, such as a digital signal processor device, a microprocessor device, various analog to digital converters, digital to analog converters, processing circuitry and other support circuits, for performing various functions including, for example, one or more of the functions described herein. The apparatus may perform control and signal processing functions of the electronic apparatus 10 among these devices according to their respective capabilities. The processor 11 thus may comprise the functionality to encode and interleave message and data prior to modulation and transmission. The processor 1 may additionally comprise an internal voice coder, and may comprise an internal data modem. Further, the processor 11 may comprise functionality to operate one or more software programs, which may be stored in memory and which may, among other things, cause the processor 11 to implement at least one embodiment including, for example, one or more of the functions described herein. For example, the processor 11 may operate a connectivity program, such as a conventional internet browser. The connectivity program may allow the electronic apparatus 10 to transmit and receive internet content, such as location-based content and/or other web page content, according to a Transmission Control Protocol (TCP), Internet Protocol (IP), User Datagram Protocol (UDP), Internet Message Access Protocol (IMAP), Post Office Protocol (POP), Simple Mail Transfer Protocol (SMTP), Wireless Application Protocol (WAP), Hypertext Transfer Protocol (HTTP), and/or the like, for example.

The electronic apparatus 10 may comprise a user interface for providing output and/or receiving input. The electronic apparatus 10 may comprise an output device 14. Output device 14 may comprise an audio output device, such as a ringer, an earphone, a speaker, and/or the like. Output device 14 may comprise a tactile output device, such as a vibration transducer, an electronically deformable surface, an electronically deformable structure, and/or the like. Output device 14 may comprise a visual output device, such as a display, a light, and/or the like. In at least one example embodiment, the apparatus causes display of information, the causation of display may comprise displaying the information on a display comprised by the apparatus, sending the information to a separate apparatus, and/or the like. For example, the apparatus may send the information to a separate display, to a computer, to a laptop, to a mobile apparatus, and/or the like. For example, the apparatus may be a server that causes display of the information by way of sending the information to a client apparatus that displays the information. In this manner, causation of display of the information may comprise sending one or more messages to the separate apparatus that comprise the information, streaming the information to the separate apparatus, and/or the like. The electronic apparatus may comprise an input device 13. Input device 13 may comprise a light sensor, a proximity sensor, a microphone, a touch sensor, a force sensor, a button, a keypad, a motion sensor, a magnetic field sensor, a camera, and/or the like. A touch sensor and a display may be characterized as a touch display. In an embodiment comprising a touch display, the touch display may be configured to receive input from a single point of contact, multiple points of contact, and/or the like. In such an embodiment, the touch display and/or the processor may determine input based, at least in part, on position, motion, speed, contact area, and/or the like. In at least one example embodiment, the apparatus receives an indication of an input. The apparatus may receive the indication from a sensor, a driver, a separate apparatus, and/or the like. The information indicative of the input may comprise information that conveys information indicative of the input, indicative of an aspect of the input indicative of occurrence of the input, and/or the like.

The electronic apparatus 10 may include any of a variety of touch displays including those that are configured to enable touch recognition by any of resistive, capacitive, infrared, strain gauge, surface wave, optical imaging, dispersive signal technology, acoustic pulse recognition, or other techniques, and to then provide signals indicative of the location and other parameters associated with the touch. Additionally, the touch display may be configured to receive an indication of an input in the form of a touch event which may be defined as an actual physical contact between a selection object (e.g., a finger, stylus, pen, pencil, or other pointing device) and the touch display. Alternatively, a touch event may be defined as bringing the selection object in proximity to the touch display, hovering over a displayed object or approaching an object within a predefined distance, even though physical contact is not made with the touch display. As such, a touch input may comprise any input that is detected by a touch display including touch events that involve actual physical contact and touch events that do not involve physical contact but that are otherwise detected by the touch display, such as a result of the proximity of the selection object to the touch display. A touch display may be capable of receiving information associated with force applied to the touch screen in relation to the touch input. For example, the touch screen may differentiate between a heavy press touch input and a light press touch input. In at least one example embodiment, a display may display two-dimensional information, three-dimensional information and/or the like.

In embodiments including a keypad, the keypad may comprise numeric (for example, 0-9) keys, symbol keys (for example, #, *), alphabetic keys, and/or the like for operating the electronic apparatus 10. For example, the keypad may comprise a conventional QWERTY keypad arrangement. The keypad may also comprise various soft keys with associated functions. In addition, or alternatively, the electronic apparatus 10 may comprise an interface device such as a joystick or other user input interface.

Input device 13 may comprise a media capturing element. The media capturing element may be any means for capturing an image, video, and/or audio for storage, display, or transmission. For example, in at least one example embodiment in which the media capturing element is a camera module, the camera module may comprise a digital camera which may form a digital image file from a captured image. As such, the camera module may comprise hardware, such as a lens or other optical component(s), and/or software necessary for creating a digital image file from a captured image. Alternatively, the camera module may comprise only the hardware for viewing an image, while a memory device of the electronic apparatus 10 stores instructions for execution by the processor 11 in the form of software for creating a digital image file from a captured image. In at least one example embodiment, the camera module may further comprise a processing element such as a co-processor that assists the processor 11 in processing image data and an encoder and/or decoder for compressing and/or decompressing image data. The encoder and/or decoder may encode and/or decode according to a standard format, for example, a Joint Photographic Experts Group (JPEG) standard format.

Figure 2:
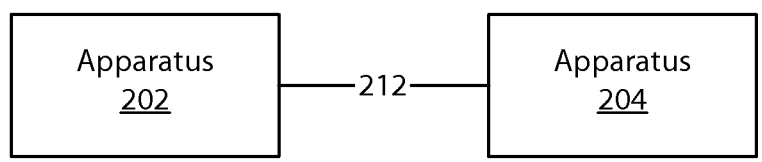
FIG. 2 is a block diagram illustrating apparatus communication according to at least one example embodiment.

FIG. 2 is a block diagram illustrating apparatus communication according to at least one example embodiment. The example of FIG. 2 is merely an example and does not limit the scope of the claims. For example, apparatus count may vary, apparatus configuration may vary, communication channels may vary, and/or the like.

In many circumstances, a user may desire to communicate by way of an electronic apparatus. For example, the user may desire to send and receive messages, send and receive audio calls, send and receive video calls, and/or the like. In many circumstances, the user may desire to engage in social interactions by way of the user's electronic apparatus. In order to facilitate such an experience, in many circumstances, it may be desirable to allow for communication between two or more apparatuses. For example, it may be desirable to allow for communication between an apparatus and a separate apparatus. In such an example, each of the apparatus and the separate apparatus may be a phone, a tablet, a computer, a laptop, an electronic apparatus, a server, a wearable apparatus, a head mounted apparatus, a projector, a near eye display, and/or the like. In at least one example embodiment, an apparatus and a separate apparatus communicate via a direct communication channel, an indirect communication channel, and/or the like. In such an example embodiment, the indirect communication channel may route communication between the apparatus and the separate apparatus by way of one or more routers, switches, hubs, distribution servers, and/or the like. In at least one example embodiment, an apparatus and a separate apparatus communicate via an indirect communication channel by way of a server. In such an example embodiment, the server may be a computer, a service platform, a repository, an application, and/or the like. For example, the server, may be configured to update an account associated with the separate apparatus such that the separate apparatus may receive information from the apparatus by way of accessing the account via the server.

In the example of FIG. 2, apparatus 202 communicates with apparatus 204 by way of communication channel 212. For example, apparatus 202 may send information to apparatus 204 by way of communication channel 212, apparatus 202 may receive information sent from apparatus 204 by way of communication channel 212, and/or the like. It should be understood that, even though the example of FIG. 2 illustrates a direct communication channel between apparatus 202 and apparatus 204, there may be intermediate apparatuses that facilitate communication between apparatus 202 and apparatus 204. For example, there may be one or more routers, hubs, switches, gateways, and/or the like, that are utilized in the communication channels between apparatus 202 and apparatus 204. In addition, there may be other separate apparatuses that apparatus 202 and/or apparatus 204 are in communication with. For example, apparatus 202 and/or apparatus 204 may be in communication with another apparatus, a separate apparatus, a different apparatus, and/or the like.

In some circumstances, a user may desire to have collaboration between apparatuses, such as between an apparatus and a separate apparatus. In some circumstances, a plurality of apparatuses may collaborate by way of local communication among the apparatuses. For example, the apparatuses may collaborate by way of low power radio frequency communication, a radio frequency communication, near field communication, inductive communication, electric field communication, Bluetooth communication, infrared communication, local area network communication, wireless local area network communication, local port communication, input/output port communication, and/or the like. In some circumstances, apparatuses may collaborate by way of non-local communication among the apparatuses. For example, the apparatuses may communicate by way of high power radio frequency communication, wide area network communication, internet communication, cellular network communication, and/or the like. In at least one example embodiment, an apparatus retains information associated with communication with a separate apparatus. For example, the apparatus may comprise information associated with identifying, communicating with, authenticating, performing authentication with, and/or the like, the separate apparatus. In this manner, the apparatus may be privileged to perform operations in conjunction with the separate apparatus that a different apparatus may lack the privilege to perform.

In at least one example embodiment, the apparatus receives information indicative of an incoming communication. For example, the apparatus may receive a radio transmission, an electrical transmission, a data transmission, and/or the like such that the apparatus is informed that a communication is incoming. An incoming communication may be a message, a call, and/or the like addressed to the apparatus and/or the user of the apparatus. For example, in circumstances where the apparatus is a telephone, the incoming communication may be a telephone call directed to a user associated with the apparatus. In many circumstances, the incoming communication may be associated with a sender of the incoming communication. A sender of the incoming communication may be a different apparatus, a user of a different apparatus, and/or the like. For example, in circumstances where the apparatus is a telephone, the sender may be a different telephone and/or a user of the different telephone. In at least one example embodiment, the incoming communication is a message, a call request, and/or the like. In at least one example embodiment, a message refers to an email, an instant message, a social media message, a text message, a multimedia message, and/or the like. In at least one example embodiment a call request refers to an audio call request, a video call request, and/or the like.

Figure 3:
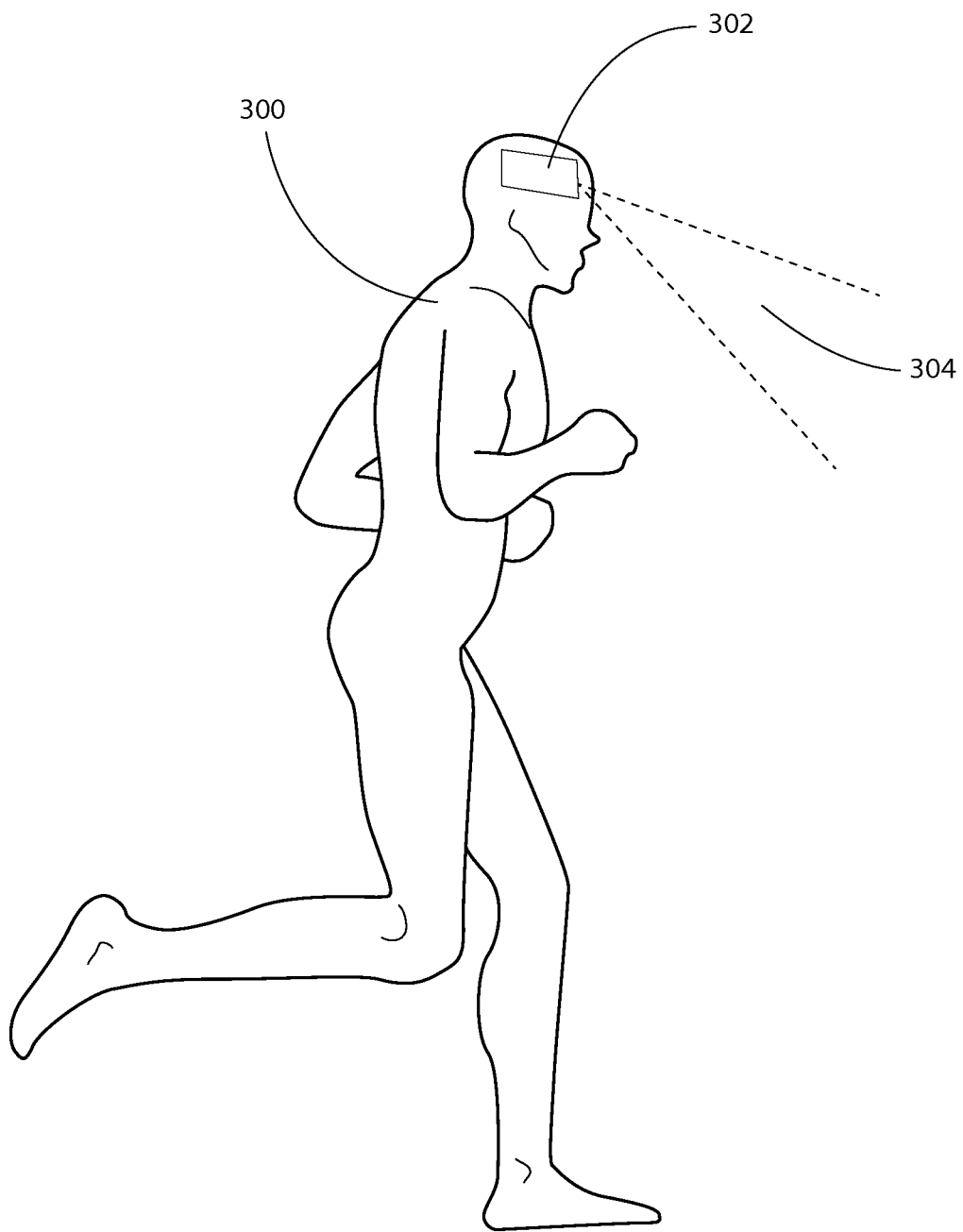
FIG. 3 is a diagram illustrating a projector display according to at least one example embodiment.

FIG. 3 is a diagram illustrating projector display according to at least one example embodiment. The example of FIG. 3 is merely an example and does not limit the scope of the claims. For example, configuration of the projector display may vary, relationship between the user and the projector display may vary, output of the see through display may vary, and/or the like.

In many circumstances, it may be desirable for a display to be a projector display. For example, it may be desirable to display information such that the information may be seen by more than one person. A projector display may refer to an apparatus that projects an image onto a surface. For example, a projector display may project a still image, a moving image, video information, camera information, and/or the like. In at least one example embodiment, a projector display comprises a laser. In at least one example embodiment, a projector display comprises a light emitting diode.

In many circumstances, it may be desirable for an apparatus comprising a projector display to be wearable by a user of the apparatus. For example, a head mounted apparatus worn by a user comprising a projector display may be configured such that the field of projection from the projector display is always presented within a field of view of a user, similar as described regarding FIGS. 5A-5D. In circumstances such as these, it may be desirable for a projector display to comprise a projection stabilization system. In this manner, information displayed by the projector may have a more stable appearance when an apparatus comprising the projector display is worn by a user. In at least one example embodiment, a projector display comprises a projection stabilization system. A projection stabilization system may be any system that stabilizes the image projected from a projector display. For example, a projector display may comprise a mechanical image stabilization system, a software image stabilization system, and/or the like.

FIG. 3 is a diagram illustrating projector display 302 according to at least one example embodiment. In the example of FIG. 3 projector display 302 is worn by user 300 such that projection 304 is projected in front of user 300. Even though the example of FIG. 3 depicts projector display 302 as being head mounted on user 300, projector display 302 may be worn by user 300 on any location, or projector display 302 may be stand alone. For example, projector display 302 may be mounted on user 300's waist, carried by user 300, or placed on a surface. Even though the example of FIG. 3 depicts projection 304 being projected in front of user 300, projection 304 may be projected in any direction.

Figure 4A:
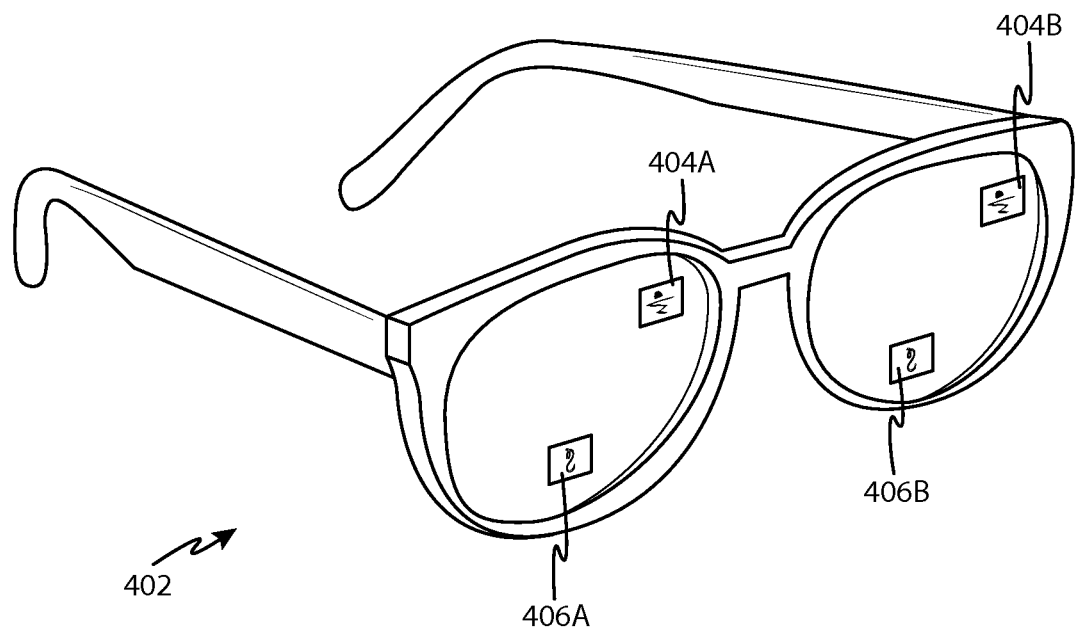
FIGS. 4A-4B are diagrams illustrating see through displays according to at least one example embodiment.
Figure 4B:
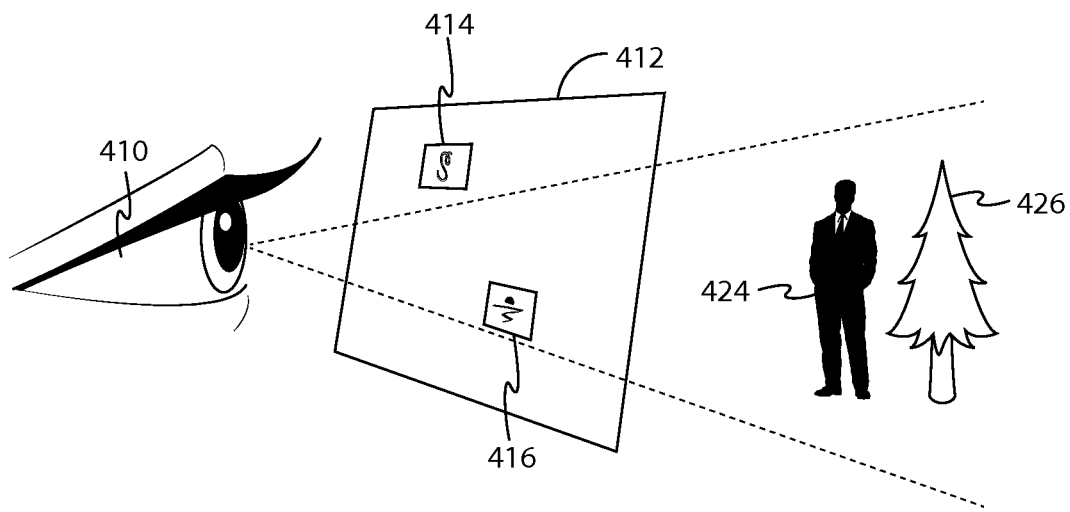

FIGS. 4A-4B are diagrams illustrating see through displays according to at least one example embodiment. The examples of FIGS. 4A-4B are merely examples and do not limit the scope of the claims. For example, configuration of the see through display may vary, relationship between the user and the see through display may vary, shape of the see through display may vary, opacity of the see through display may vary, and/or the like.

In some circumstances, it may be desirable for a display to be a see through display. In at least one example embodiment, a see through display is a display that presents information to a user, but through which objects on an opposite side of the display from the user may be seen. A see through display may be comprised by a window, a windshield, a visor, glasses, a head mounted display, and/or the like. A head mounted display may, for example, be a display that is head mountable, a display that is coupled to an element that is wearable at a location on and/or proximate to the head of a user, a display that is wearable at a location on and/or proximate to the head of a user, and/or the like.

FIG. 4A is a diagram illustrating display 402 according to at least one example embodiment. In the example of FIG. 4A, display 402 is illustrated as a see through display, though display 402 may be any type of display. For example, display 402 may be a non-see through display. In at least one example embodiment, a see through display is a near eye display. A near eye display may be a see through display that is positioned proximate to an eye of the user. The example of FIG. 4A illustrates display 402 as glasses that comprise a near eye display in each lens. In the example of FIG. 4A, the right near eye display is displaying information 404A and 406A, and the left near eye display is displaying information 404B and 406B. In at least one example embodiment, information 404A may be associated with information 404B. For example, the content of information 404A may be identical to content of information 404B. In some circumstances, even though the content may be identical between 404A and 404B, position of information 404A on the right near eye display may vary from position of information 404B on the left near eye display. In this manner, the apparatus may vary position of information between the left near eye display and right near eye display to vary the parallax of the information perceived by the user. In this manner, the apparatus may vary the perceived depth of the information by the user.

FIG. 4B is a diagram illustrating see through display 412 according to at least one example embodiment. In at least one example embodiment, displaying information on a see through display so that the information corresponds with one or more objects viewable through the see through display is referred to as augmented reality. In the example of FIG. 4B, user 410 may perceive objects 424 and 426 through see through display 412. In at least one example embodiment, the see through display may display information to the user. For example, display 412 may display information 414 and information 416. Information 414 and information 416 may be positioned on display 412 such that the information corresponds with one or more objects viewable through see through display 412, such as object 424. In such an example, information 414 may be associated with, identify, and/or the like, object 424. For example, information 414 may indicate an identity of object 424. In at least one example embodiment, display 412 may be comprised by a head mounted display.

FIGS. 5A-5D are diagrams illustrating fields of view of a display according to at least one example embodiment. The examples of FIGS. 5A-5D are merely examples and do not limit the scope of the claims. For example, the size of the fields of view may vary, the shape of the fields of view may vary, the location of the fields of view may vary, and/or the like.

In many circumstances, when a user views information displayed by an apparatus, a particular field of view may be visible to the user. For example, when information is projected onto a surface from a projector display, a particular field of view will be visible with respect to the projected image based on the position of the projector display in relation to the user, the orientation of projector display, and/or the like. In another example, when a viewer views an image on a see through display, a particular field of view will be visible through the see through display based on the position of the see through display in relation to the user, the orientation of the see through display, and/or the like. In at least one example embodiment, the display is a projector display and the field of view of the display is a physical region in which information projected by the projector display appears. In at least one example embodiment, the field of view of the display is a field of projection of the projector display. Field of projection may refer to the area on a surface where projected information is projected. In at least one example embodiment, the display is a near eye display and the field of view of the display is a physical region that is viewable through the near eye display.

Figure 5A:
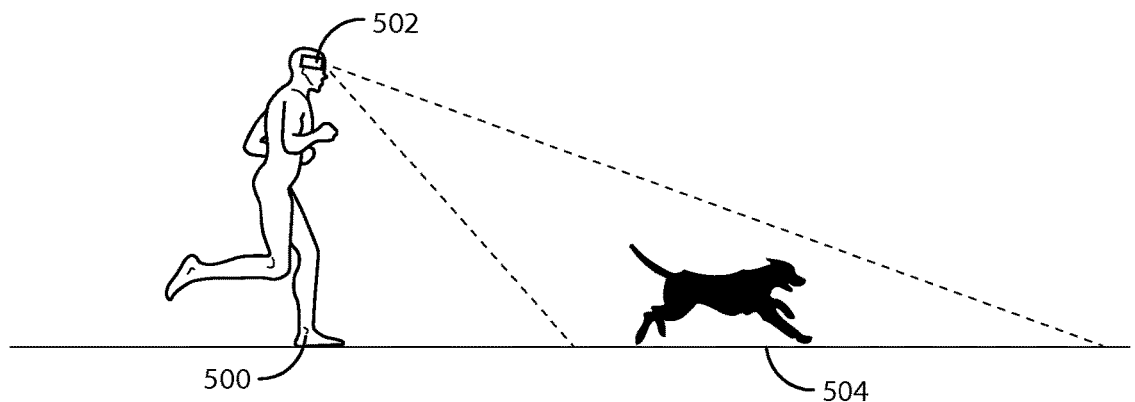
FIGS. 5A-5D are diagrams illustrating fields of view of a display according to at least one example embodiment.
Figure 5B:
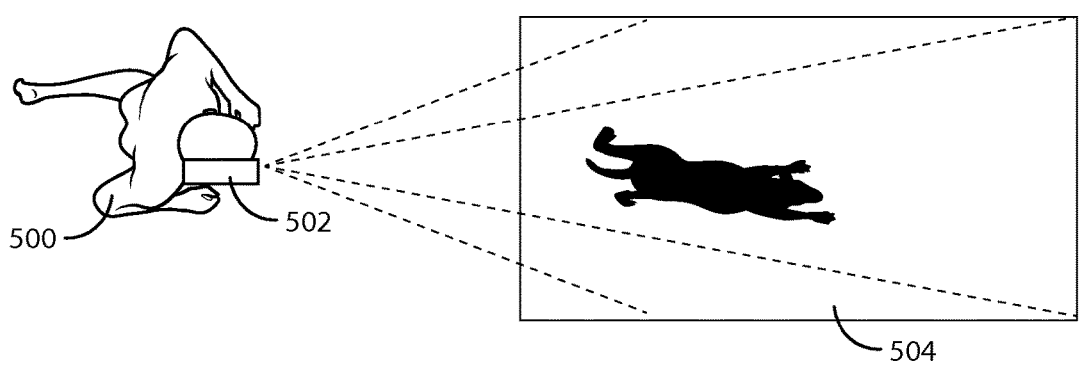

The example of FIGS. 5A-5B illustrates user 500 wearing an apparatus 502. FIG. 5A is a side view and FIG. 5B is a top down view of the same example. In the example of FIGS. 5A-5B, apparatus 502 is illustrated as a projector display, but apparatus 502 may be any type of display, such as a near eye display, a see through display, and/or the like. The example of FIGS. 5A-5B illustrates field of view 504. Field of view 504 is a field of view of display 502. For example, in circumstances where apparatus 502 is a projector display, field of view 504 may be the field of projection of apparatus 502. In another example, in circumstances where apparatus 502 is a near eye display, field of view 504 may be the physical region that is viewable through apparatus 502.

In at least some circumstances, it may be desirable to determine the apparatus location. For example, the apparatus may display information based, at least in part, on the current location of the apparatus, determine the location of a user, based at least in part, on the current location of the apparatus, and/or the like. In at least one example embodiment, the apparatus receives apparatus location information associated with the apparatus. Apparatus location information may comprise information indicative of the position of the apparatus on Earth. For example, the apparatus location information may comprise geographic location information. The apparatus location information may comprise location information with respect to another location. For example the apparatus location information may comprise relative location information in relation to predetermined reference point, a beacon, with respect to another apparatus, with respect to a landmark, and/or the like. For example, the apparatus may receive the apparatus location information from at least one memory, from another apparatus, from one or more sensors configured to sense the location of the apparatus, and/or the like. In at least one example embodiment, apparatus location information is location sensor information. In at least one example embodiment, location sensor information may be information received from a global positioning system sensor, radio triangulation, a magnetometer sensor, a gyroscope sensor, an accelerometer sensor, an optical sensor, an imaging sensor, and/or the like. In at least one example embodiment, determination of an apparatus location is based, at least in part, on location sensor information.

In at least some circumstances, it may be desirable to determine the apparatus orientation. For example, the apparatus may display information based, at least in part, on the current orientation of the apparatus. In at least one example embodiment, the apparatus receives apparatus orientation information associated with the apparatus. For example, the apparatus may receive information associated with movement of the apparatus, the user's head, body, and/or the like. Apparatus orientation information may refer to information indicative of one or more movements of the apparatus, information indicative of the position of the apparatus, information indicative of a rotational orientation of the apparatus, information indicative of a spatial orientation of the apparatus, and/or the like. For example, the apparatus may receive the apparatus orientation information from at least one memory, from another apparatus, from one or more sensors configured to sense an orientation of the user and/or the apparatus, and/or the like. In at least one example embodiment, apparatus orientation information is orientation sensor information. For example, the orientation sensor information may provide information indicative of an orientation of the apparatus, the user's head, the user's body, and/or the like, and/or provide information indicative of movement of the sensed apparatus, head, body, and/or the like. In at least one example embodiment, orientation sensor information may be information received from a magnetometer sensor, a gyroscope sensor, an accelerometer sensor, an orientation sensor, a myoelectric sensor, an optical sensor, an imaging sensor, a sensor configured to sense information associated with movement of the apparatus, a head, a body, and/or the like. For example, one or more sensors may be utilized to sense information indicative of an apparatus movement, an apparatus orientation, a head movement, a head orientation, a body movement, a body orientation, and/or the like. In at least one example embodiment, determination of an apparatus orientation is based, at least in part, on orientation sensor information.

In at least one example embodiment, an apparatus determines an apparatus movement of the apparatus. For example, the apparatus may determine, calculate, extrapolate, infer, and/or the like apparatus movement information based, at least in part, on the orientation sensor information. Apparatus movement information may comprise information indicative of apparatus deviation direction, magnitude of an apparatus movement, and or the like. Deviation direction may identify a direction of movement from an orientation to a different orientation, from a predetermined orientation to a different orientation, from a neutral orientation to a different orientation, and/or the like. Magnitude of a movement may identify the distance of movement between an orientation before a movement and a different orientation after a movement. For example, the apparatus may move from a level orientation to a tilted orientation with a magnitude of 50 millimeters, a magnitude of 10-degrees with respect to a horizontal plane, and/or the like.

In at least one example embodiment, an apparatus determines a head movement of the user. For example, the apparatus may determine, calculate, extrapolate, infer, and/or the like head movement information based, at least in part, on the orientation sensor information. In at least one example embodiment, head movement information comprises information indicative of head deviation direction. In at least one example embodiment, head movement information comprises information indicative of the magnitude of the head movement. For example, the user's head may move from a forward looking orientation to a rightward looking orientation with a magnitude of 60 degrees with respect to a vertical plane.

In at least one example embodiment, an apparatus determines a body movement of the user. For example, the apparatus may determine, calculate, extrapolate, infer, and/or the like body movement information based, at least in part, on the orientation sensor information. In at least one example embodiment, body movement information comprises information indicative of body deviation direction. In at least one example embodiment, body movement information comprises information indicative of the magnitude of the body movement. For example, the user's body may move from a seated orientation to a standing orientation with a magnitude of 1 meter.

Figure 5C:
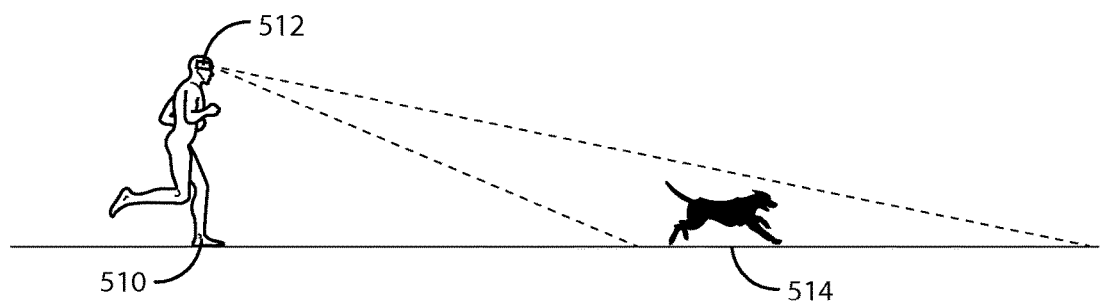
Figure 5D:
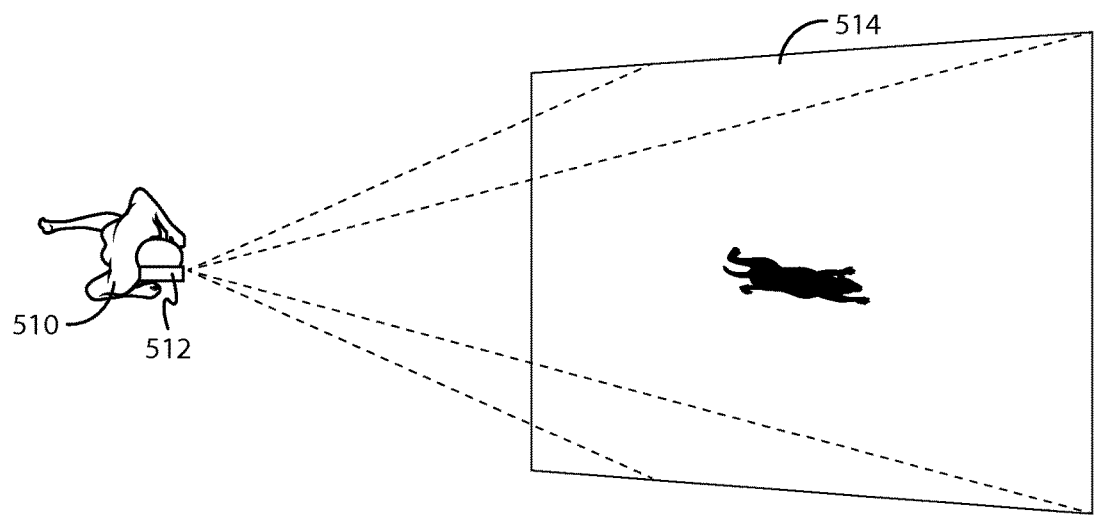

As the location and/or orientation of a display apparatus varies, different fields of view may be visible based, at least in part, on the location and/or orientation of the display apparatus. The example of FIGS. 5C-5D illustrates user 510 wearing an apparatus 512. FIG. 5C is a side view and FIG. 5D is a top down view of the same example. In the example of FIGS. 5C-5D, apparatus 512 is illustrated as a projector display, but apparatus 512 may be any type of display, such as a near eye display, a see through display, and/or the like. The example of FIGS. 5C-5D illustrates field of view 514. Field of view 514 is a field of view of display 512. For example, in circumstances where apparatus 512 is a projector display, field of view 514 may be the field of projection of apparatus 512. In another example, in circumstances where apparatus 502 is a near eye display, field of view 514 may be the physical region that is viewable through apparatus 512. It can be seen that field of view 514 is at a position further in front of user 510 than the position of field of view 504 is positioned in front of user 500 of FIGS. 5A-5B. Even though field of view 514 is illustrated as a field of view associated with apparatus 512, field of view 512 may be a field of view associated with any apparatus, such as apparatus 502. For example, user 500 may reposition his head such that apparatus 502 has a field of view similar to that of field of view 514.

FIGS. 6A-6D are diagrams illustrating an exercise plan according to at least one example embodiment. The examples of FIGS. 6A-6D are merely examples and do not limit the scope of the claims. For example, the type of exercise may vary, the exercise duration may vary, the number of exercises may vary, and/or the like.

In modern times, a user of a device may carry, wear, and/or the like an electronic apparatus when performing exercise. In circumstances such as these, it may be desirable for the user to interact with the apparatus during performance of the exercise. For example, it may be desirable for the apparatus to indicate information that may be related to the exercise to the user. For instance, the apparatus may indicate an exercise plan to the user. An exercise plan may refer to information related to an exercise routine that may be performed by a user.

In at least one example embodiment, an exercise plan comprises information indicative of a particular type of exercise. In at least one example embodiment, a type of exercise designates a particular activity to be performed by a user. For example, the type of exercise may comprise running, walking, and/or the like.

In some circumstances, it may be desirable for the user to perform an exercise in relation to one or more locations. For example, it may be desirable for the user to perform a particular exercise at a particular location, to perform a particular exercise along a particular route, and/or the like. In at least one example embodiment, the exercise plan correlates exercise instruction information with location information. In at least one example embodiment, location information comprises information indicative of an exercise route segment. An exercise route segment may refer to a portion of an exercise plan where a particular exercise is to be performed. For example, if the exercise to be performed is walking, the route segment may indicate a particular street, sidewalk, trail, and/or the like where the walking should be performed. In at least one example embodiment, exercise instruction information comprises information that designates at least one exercise activity. For example, exercise instruction information may designate walking, running, jumping, and/or the like. In at least one example embodiment, the exercise activity comprises at least one of walking, walking with a particular characteristic, running, running with a particular characteristic, jumping, hopping, bounding, skipping, and/or the like. In at least one example embodiment, the particular characteristic indicates a manner of leg movement. For example, the particular characteristic may indicate running with high knees, high heels, long strides, short strides, and/or the like.

There are various manners in which an exercise plan may be embodied by an apparatus. For instance, an exercise plan may comprise a data structure, a formatted table, a user readable list, and/or the like that correlates a particular type of exercise with a particular location. An exercise plan may be retrieved from a repository, generated by a user profile, configured by a user of the apparatus, generated based, at least in part, on a previous exercise plan, may be created ad hoc as the exercise progresses, and/or the like.

FIG. 6A illustrates a set of records comprised by an exercise plan. The exercise plan in the example of FIG. 6A comprises exercise route segments 602, 604, and 606; as well as exercise instruction information 612, 614, and 616. In the example of FIG. 6A, route segment 602 is correlated with exercise instruction information 612, route segment 604 is correlated with exercise instruction information 614, and route segment 606 is correlated with exercise instruction information 616. In this manner, an apparatus may determine from the exercise plan illustrated in FIG. 6A that a particular exercise activity, for example an exercise activity indicated by exercise instruction information 612 should be performed at a particular location, such as a location indicated by exercise route segment 602.

In some circumstances, it may be desirable for an exercise plan to designate an exercise pace. For example, a user of an apparatus may desire to begin an exercise routine at a moderate pace, such as for a warm up, perform a later part of a workout at a strenuous pace, and finish the workout at a slower pace, such as for a cool down. In circumstances such as these, the exercise plan may indicate that particular exercise route segments should be performed at particular paces. Exercise pace may refer to the rate at which an exercise activity is performed. For example, if the exercise activity is running, an exercise pace may indicate a rate at which a distance should be covered. For instance an exercise pace may indicate a rate of 10 minutes per kilometer, 5 minutes per kilometer, 7 minutes per mile, and/or the like. In at least one example embodiment, exercise instruction information designates an exercise pace for at least one exercise activity.

FIG. 6B illustrates a set of records comprised by an exercise plan. The exercise plan in the example of FIG. 6B comprises exercise route segments 622, 624, and 626; as well as exercise paces 632, 634, and 636. In the example of FIG. 6B, route segment 622 is correlated with exercise pace 632, route segment 624 is correlated with exercise pace 634, and route segment 626 is correlated with exercise pace 636. In this manner, an apparatus may determine from the exercise plan illustrated in FIG. 6B that a particular exercise should be performed with a particular exercise pace, for example, an exercise pace indicated by exercise pace 632, and at a particular location, such as a location indicated by exercise route segment 622.

In some circumstances, it may be desirable for an exercise plan to designate a physiological state. Physiological state may refer to a measurable physical condition of a user, such as heart rate, temperature, breathing rate, and/or the like. For example, a user of an apparatus may desire to reach various physiological states at different points during the exercise routine. In circumstances such as these, the exercise plan may indicate at what exercise route segments should be performed at physiological states. For example, if the exercise activity is running, a physiological state may indicate a particular physical condition at which an exercise activity should be performed. For example, a physiological condition may indicate a heart rate of 140 beats per minute, a breathing rate of 60 breaths per minute, and/or the like. In at least one example embodiment, exercise instruction information comprises information that designates a physiological state of the user.

FIG. 6C illustrates a set of records comprised by an exercise plan. The exercise plan in the example of FIG. 6C comprises exercise route segments 642, 644, and 646; as well as physiological states 652, 654, and 656. In the example of FIG. 6C, route segment 642 is correlated with physiological state 652, route segment 644 is correlated with physiological 654, and route segment 646 is correlated with physiological state 656. In this manner, an apparatus may determine from the exercise plan illustrated in FIG. 6C that a particular exercise should be performed at a particular physiological state, for example a physiological state indicated by physiological state 652, should be performed at a particular location, such as a location indicated by exercise route segment 642. For example, physiological state 652 may indicate a physiological state of below 140 beats per minute should be maintained, while exercise route segment 642 may indicate a beginning segment of a running trail. Similarly, physiological state 644 may indicate a physiological state of above 140 beats per minute should be maintained, while exercise route segment 654 may indicate a middle segment of a running trail.

In at least some circumstances, it may be desirable for exercise instruction information in an exercise plan to correlate more than one type of exercise instruction information with an exercise route segment. For example, it may be desirable for, an exercise plan may indicate a particular exercise route segment to be performed with several defined parameters. For example, an exercise plan may indicate a particular exercise route segment to perform a particular exercise activity with a particular pace at a particular physiological state.

FIG. 6D illustrates a set of records comprised by an exercise plan. The exercise plan in the example of FIG. 6D comprises exercise route segments 662, 664, and 666; exercise activities 672, 674, and 676; exercise paces 682, 684, and 686; and physiological states 692, 694, and 696. In the example of FIG. 6D, route segment 662 is correlated with exercise activity 672, exercise pace 682, and physiological state 692; route segment 664 is correlated with exercise activity 674, exercise pace 684, and physiological state 694; and route segment 666 is correlated with exercise activity 676, exercise pace 686, and physiological state 696. In this manner, an apparatus may determine from the exercise plan illustrated in FIG. 6D that a particular exercise activity should be performed at a particular exercise pace and a particular physiological state at a particular location, similar as described regarding FIGS. 6A-6C.

FIGS. 7A-7F are diagrams illustrating display of exercise instruction information according to at least one example embodiment. The examples of FIGS. 7A-7F are merely examples and do not limit the scope of the claims. For example, the type of exercise instruction information may vary, the type of display may vary, the location in which information is displayed may vary, and/or the like.

As previously described, it may be desirable for a user to interact with an electronic apparatus while performing exercise. In circumstances such as these, it may be desirable for the apparatus to display information related to exercise instruction information. For example, an apparatus may display information related to an exercise plan, similar as described regarding FIGS. 6A-6D. For instance, the apparatus may cause display of an exercise indicator that indicates exercise instruction information in relation to physical objects, such as a road, a trail, obstacles, and/or the like. An exercise indicator may refer to graphical information that represents an exercise activity. For example, an exercise indicator may comprise text, symbols, and/or the like that represent walking, running, jumping, and/or the like. In at least one example embodiment, causation of display of the exercise indicator is performed such that the exercise indicator is perceivable within the field of view of the display. In at least one example embodiment, the apparatus causes display of an exercise indicator that indicates exercise instruction information that corresponds with a portion of an exercise plan. For example, an exercise indicator may indicate exercise instruction information 612 which corresponds with exercise route segment 602 of FIG. 6A.

Figure 7A:
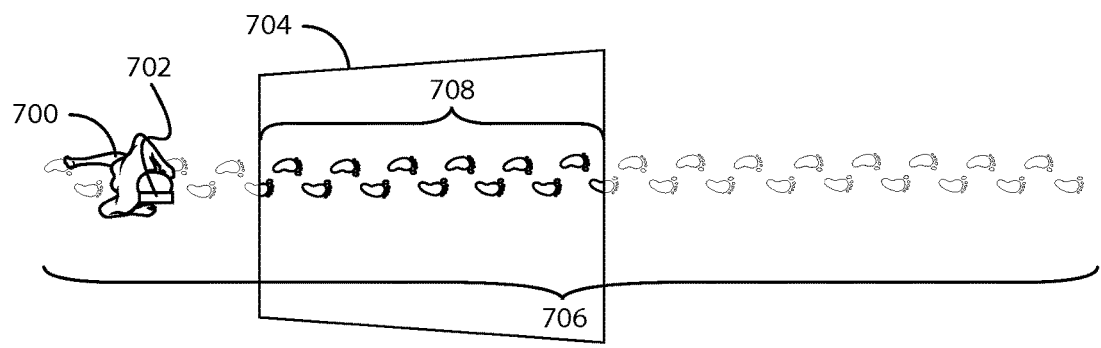
FIGS. 7A-7F are diagrams illustrating display of exercise instruction information according to at least one example embodiment.

FIG. 7A illustrates user 700 wearing apparatus 702 in a manner that a display comprised by apparatus 702 is oriented in a downward direction from the perspective of user 700, similar as described regarding FIGS. 5A-5B. Apparatus 702 may comprise any type of display, such as a display similar as described regarding FIG. 3, FIGS. 4A-4B, and/or the like. In the example of FIG. 7A, apparatus 702 has a field of view of the display 704, and user 700 is performing an exercise activity related to exercise route segment 706. Even though exercise route segment is 706 is illustrated as a series of footprints, it should be understood that exercise route segment 706 may be represented with other symbols, text, graphics, and/or the like. In the example of FIG. 7A, apparatus 702 is causing display of exercise indicator 708 within field of view of the display 704. Even though exercise indicator 708 is illustrated as a series of footprints, it should be understood that exercise indicator 708 may be displayed as other symbols, text, graphics, and/or the like. It should be understood that exercise indicator 708 corresponds with a portion of exercise route segment 706. It can be seen that apparatus 702 is causing display of exercise indicator 708 in the field of view of the display 704 so that exercise indicator 708 is observable by the user.

Figure 7B:
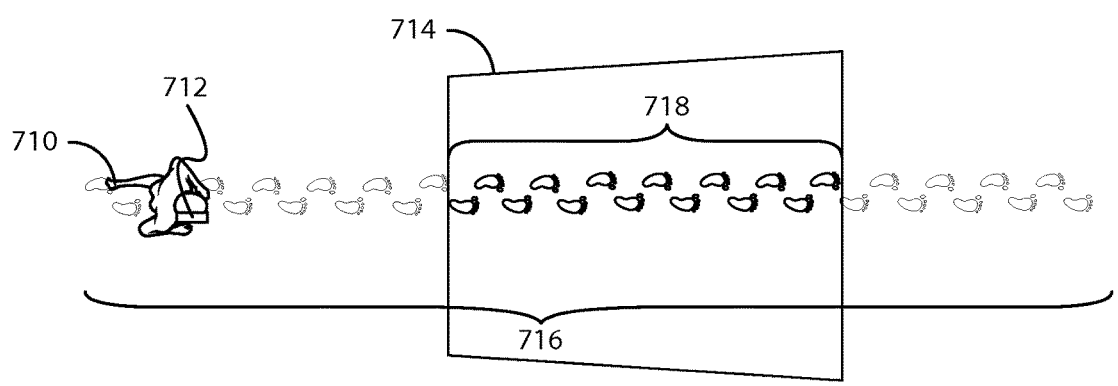

FIG. 7B illustrates user 710 wearing apparatus 712 in a manner that a display comprised by apparatus 712 is oriented in a downward direction from the perspective of user 710 similar as described regarding FIGS. 5C-5D. Apparatus 712 may comprise any type of display, such as a display similar as described regarding FIG. 3, FIGS. 4A-4B, and/or the like. In the example of FIG. 7B, apparatus 712 has a field of view of the display 714, and user 710 is performing an exercise activity related to exercise route segment 716. Even though exercise route segment is 716 is illustrated as a series of footprints, it should be understood that exercise route segment 716 may be represented with other symbols, text, graphics, and/or the like. In the example of FIG. 7B, display 712 is causing display of exercise indicator 718 within field of view of the display 714. Even though exercise indicator 718 is illustrated as a series of footprints, it should be understood that exercise indicator 718 may be displayed as other symbols, text, graphics, and/or the like. It should be understood that exercise indicator 718 is corresponds with a portion of exercise route segment 716. It can be seen that apparatus 722 is causing display of exercise indicator 718 in the field of view of the display 714 so that exercise indicator 718 is observable by the user.

In at least one example embodiment, the apparatus determines a portion of the exercise plan that corresponds with the location of the user. For example, the apparatus may determine the location of the user similar as described regarding FIG. 12. In this manner, the field of view of the apparatus may vary based, at least in part, on the apparatus orientation. For example, an apparatus may have a field of view similar as described regarding field of view of the display 704 of FIG. 7A when the apparatus has one orientation. The apparatus may have a field of view similar as described regarding field of view of the display 714 of FIG. 7B when the apparatus has a different orientation.

Figure 7C:
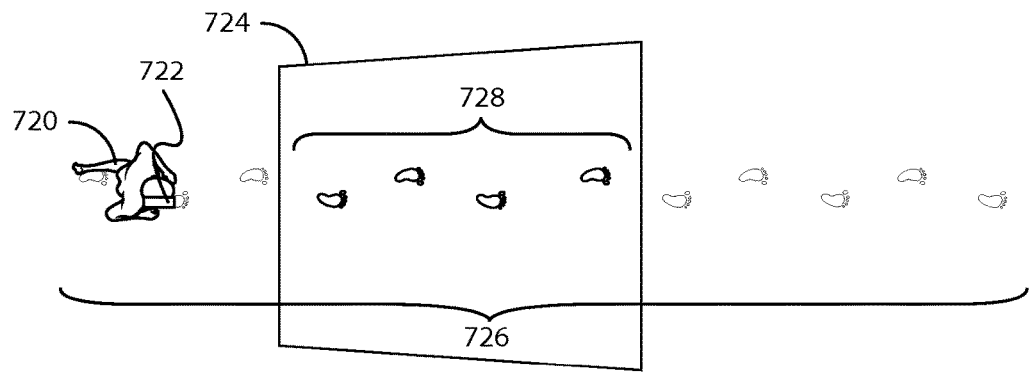

FIG. 7C illustrates user 720 wearing apparatus 722 comprising a display. Apparatus 722 may comprise any type of display, such as a display similar as described regarding FIG. 3, FIGS. 4A-4B, and/or the like. In the example of FIG. 7C, apparatus 722 has a field of view of the display 724, and user 720 is performing an exercise activity related to exercise route segment 726. Even though exercise route segment is 726 is illustrated as a series of footprints, it should be understood that exercise route segment 726 may be represented with other symbols, text, graphics, and/or the like. In the example of FIG. 7C, apparatus 722 is causing display of exercise indicator 728 within field of view of the display 724. Even though exercise indicator 728 is illustrated as a series of footprints, it should be understood that exercise indicator 728 may be displayed as other symbols, text, graphics, and/or the like. It should be understood that exercise indicator 728 corresponds with a portion of exercise route segment 726. It can be seen that apparatus 722 is causing display of exercise indicator 728 in the field of view of the display 724 so that exercise indicator 728 is observable by the user.

In at least one example embodiment, the exercise indicator comprises footfall indicators and indicates exercise pace by way of distance between the footfall indicators. For example, the footprints illustrated as exercise indicator 718 of FIG. 7B may represent footfall indicators such that the distance between the footprints indicates exercise pace. In at least one example embodiment, a long distance between footfall indicators is indicative of a quicker exercise pace than a short distance between footfall indicators. In at least one example embodiment, a short distance between footfall indicators is indicative of a slower exercise pace than a long distance between footfall indicators. For example, it can be seen that the footprints illustrated as exercise indicator 718 of FIG. 7B have a shorter distance between them than the footprints illustrated as exercise indicator 728 of FIG. 7C. In this manner, exercise pace may be proportional to the distance between footfall indicators such that exercise indicator 728 may indicate a quicker exercise pace than exercise indicator 718.

In many circumstances, it may be desirable for an apparatus to display at least one additional exercise indicator. For example, a user of the apparatus may identify the end of an exercise route segment is approaching, the beginning of an exercise route segment is approaching, and/or the like, by displaying one or more additional exercise indicator. In another example, an additional exercise indicator may identify an additional exercise activity. In at least one example embodiment, an exercise plan comprises at least one additional exercise activity. In at least one embodiment, the additional exercise activity comprises walking, walking with a particular characteristic, running, running with a particular characteristic, jumping, hopping, bounding, bouncing, skipping, and/or the like.

Figure 7D:
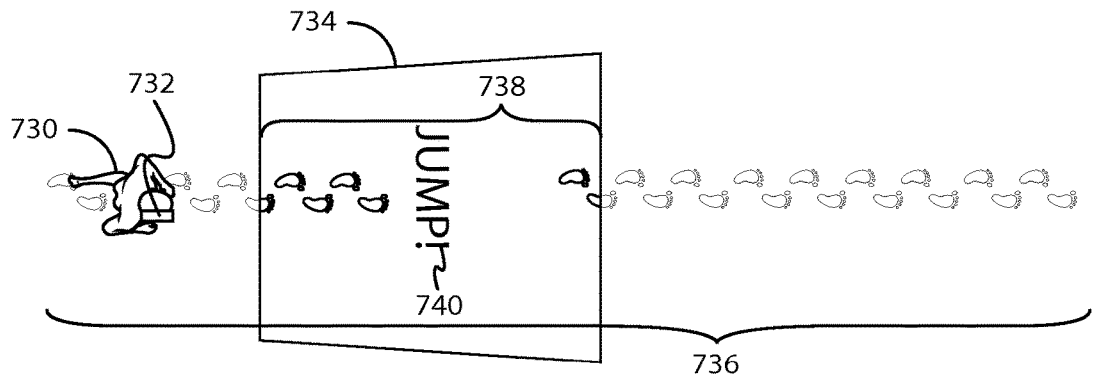

FIG. 7D illustrates user 730 wearing apparatus 732 comprising a display. Apparatus 732 may comprise any type of display, such as a display similar as described regarding FIG. 3, FIGS. 4A-4B, and/or the like. In the example of FIG. 7D, apparatus 732 has a field of view of the display 734, and user 730 is performing an exercise activity related to exercise route segment 736. Even though exercise route segment is 736 is illustrated as a series of footprints, it should be understood that exercise route segment 736 may be represented with other symbols, text, graphics, and/or the like. In the example of FIG. 7D, apparatus 732 is causing display of exercise indicator 738 within field of view of the display 734. Even though exercise indicator 738 is illustrated as a series of footprints and text, it should be understood that exercise indicator 738 may be displayed as other symbols, text, graphics, and/or the like. It should be understood that exercise indicator 738 corresponds with a portion of exercise route segment 736. It can be seen that apparatus 732 is causing display of exercise indicator 738 in the field of view of the display 734 so that exercise indicator 738 is observable by the user. In the example of FIG. 7D, apparatus 732 is causing display of additional exercise indicator 740 within field of view of the display 734. Even though additional exercise indicator 740 is illustrated as text, it should be understood that additional exercise indicator 740 may be displayed as symbols, other text, graphics, and/or the like. In the example of FIG. 7D, the portion of the exercise plan indicated by exercise indicators 738, and 740 provides more exercise variety than the portion of the exercise plan indicated by exercise indicator 708 of FIG. 7A.

In many circumstances, it may be desirable for an apparatus to receive physiological sensor information. For example, it may be desirable for the apparatus to determine the physiological state of a user. In circumstances such as these, the apparatus may cause the display of information indicative of the physiological state of the user. For example, apparatus may determine the heart rate, temperature, and/or the like from a heart rate sensor, a thermometer, a temperature sensor, and/or the like, and display the heart rate, temperature, and/or the like on a display for the user of the apparatus to view. In another example, the apparatus may determine that the physiological state of the user substantially exceeds another physiological state of the user designated by exercise instruction information. Substantially exceeding may refer to exceeding beyond a predetermined threshold. In this manner, the apparatus may utilize the physiological data to modify an exercise plan such that the user no longer exceeds the predetermined threshold. For example, the predetermined threshold may be a heart rate threshold for fat loss, a heart rate threshold for cool down, a respiratory threshold associated with endurance running, and/or the like.

In many circumstances, it may be desirable for an apparatus to determine an exercise pace of the user. For example, the apparatus may determine the exercise pace of the user based, at least in part, on a change of location of the apparatus, the speed of the apparatus, and/or the like. In at least one example embodiment, the apparatus causes display of information indicative of the exercise pace of the user. In at least one example embodiment, the information indicative of the pace may be graphical information, textual information, and/or the like. For example, the information indicative of the pace may comprise text that represents the pace. In another example, the information indicative of the pace may comprise an icon that indicates the pace. In at least one example embodiment, the apparatus determines the representation of the exercise indicator such that the exercise indicator indicates the pace. For example, the apparatus may indicate the pace by way of distance between footfalls of an exercise indicator. In such an example, a larger distance between footfalls may indicate a faster pace than a shorter distance between footfalls.

In some circumstances, it may be desirable to change a pace of the user. For example, the apparatus may determine that the exercise pace of the user substantially exceeds an exercise pace designated by exercise instruction information. In this manner, the apparatus may utilize the exercise pace of the user to modify an exercise plan such that the user no longer exceeds the predetermined threshold. For example, the exercise pace of the user may exceed an exercise pace predetermined by the user, and the apparatus may modify the exercise plan in a manner that the exercise pace is decreased. In such circumstances, it may be desirable for the apparatus to influence of the pace to the user. For example, the apparatus may change the type of exercise in a manner that invokes the user to achieve the changed pace. For example, the apparatus may slow the pace of the user by providing an exercise indicator that indicates a slower exercise, a more strenuous exercise, and/or the like. In such an example, the apparatus may shorten the distance between footfall indicators displayed on a display to slow the exercise pace of the user.

Figure 7E:
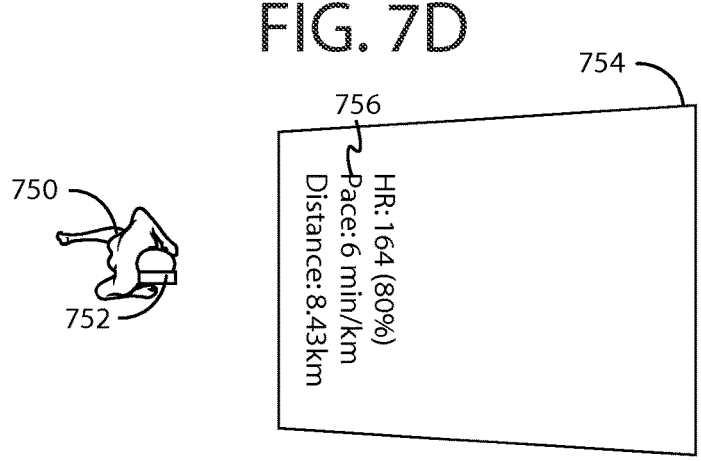

FIG. 7E illustrates user 750 wearing apparatus 752 comprising a display. Apparatus 752 may comprise any type of display, such as a display similar as described regarding FIG. 3, FIGS. 4A-4B, and/or the like. In the example of FIG. 7E, apparatus 752 has a field of view of the display 754. In the example of FIG. 7E, apparatus 752 is causing display of information 756 within field of view of the display 754. Even though information 756 is illustrated as text, it should be understood that information 756 may be displayed as other text, symbols, graphics, and/or the like. As can be seen in the example of FIG. 7E, user 750 may perceive information that allows user 750 to adjust his exercise pace, increase his heart rate, decrease his respiratory rate, and/or the like.

In some circumstances, it may be desirable for an apparatus to identify an alternative exercise route segment. An alternative exercise route segment may refer to an optional route segment that may be selected by the user. For example, the apparatus may display information about an alternative exercise route segment to the user. In this manner, the user may decide to continue with an existing exercise route segment, or choose to follow the alternate exercise route segment. In at least one example embodiment, location information comprises information indicative of an alternative exercise route segment, wherein the alternative exercise route segment identifies an optional exercise route segment that may be selected by the user.

Figure 7F:
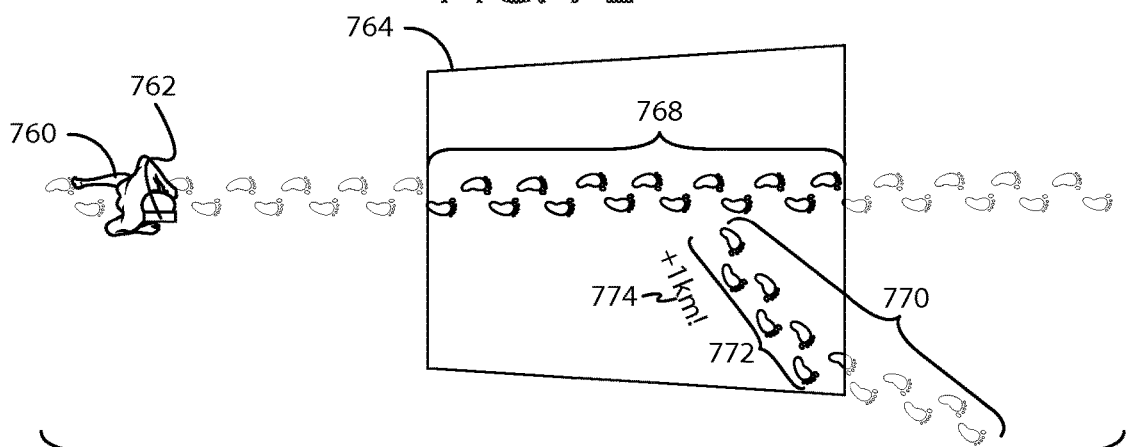

FIG. 7F illustrates user 760 wearing apparatus 762 comprising a display. Apparatus 762 may be any type of display, such as a display similar as described regarding FIG. 3, FIGS. 4A-4B, and/or the like. In the example of FIG. 7F, apparatus 762 has a field of view of the display 764, and user 760 is performing an exercise activity related to exercise route segment 766. Even though exercise route segment is 766 is illustrated as a series of footprints, it should be understood that exercise route segment 766 may be represented with other symbols, text, graphics, and/or the like. In the example of FIG. 7F, apparatus 762 is causing display of exercise indicator 768 within field of view of the display 764. Even though exercise indicator 768 is illustrated as a series of footprints and text, it should be understood that exercise indicator 768 may be displayed as other symbols, text, graphics, and/or the like. It should be understood that exercise indicator 768 corresponds with a portion of exercise route segment 766. It can be seen that apparatus 762 is causing display of exercise indicator 768 in the field of view of the display 764 so that exercise indicator 768 is observable by the user. Additionally, the example of FIG. 7F illustrates alternative exercise route segment 770. Even though exercise route segment is 770 is illustrated as a series of footprints, it should be understood that exercise route segment 770 may be represented with other symbols, text, graphics, and/or the like. In the example of FIG. 7F, apparatus 762 is causing display of exercise indicator 772 within field of view of the display 764. Even though exercise indicator 772 is illustrated as a series of footprints, it should be understood that exercise indicator 772 may be displayed as other symbols, text, graphics, and/or the like. It should be understood that exercise indicator 772 corresponds with a portion of alternative exercise route segment 770. It can be seen that apparatus 762 is causing display of exercise indicator 772 in the field of view of the display 764 so that exercise indicator 772 is observable by the user. In the example of FIG. 7F, apparatus 762 is causing display of alternative exercise route information indicator 774 within field of view of the display 764. Alternative exercise route segment information indicator 774 displays additional information related to alternative exercise route segment 770. In the example of FIG. 7F, alternative exercise route segment information indicator 774 represents that alternative exercise route segment 770 is one kilometer longer than exercise route segment 766, though it should be understood that alternative exercise route segment information indicator 774 may represent any information about alternative exercise route segment 770. For example, alternative exercise route segment information indicator 774 may represent that alternative route segment 770 will take longer to complete, has a different difficulty level, and/or the like.

Figure 8:
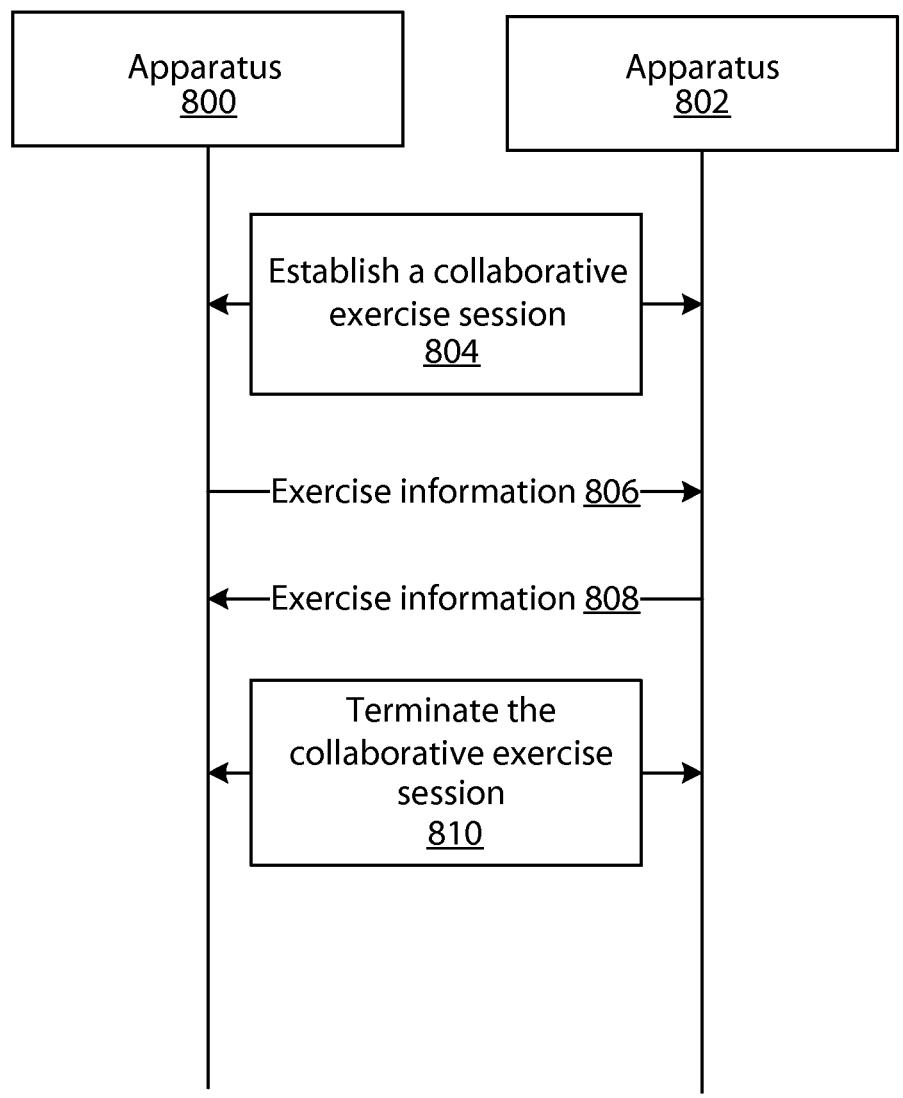
FIG. 8 is an interaction diagram illustrating activities associated with a collaborative exercise session according to at least one example embodiment.

FIG. 8 is an interaction diagram illustrating activities associated with a collaborative exercise session according to at least one example embodiment. In at least one example embodiment, there is a set of operations that corresponds with, at least some of, the activities of FIG. 8. For example, there may be a set of operations associated with activities of one or more apparatuses of FIG. 8. An apparatus, for example electronic apparatus 10 of FIG. 1, or a portion thereof, apparatus 202 of FIG. 2, or a portion thereof, apparatus 204 of FIG. 2, or a portion thereof, apparatus 302 of FIG. 3, or a portion thereof, apparatus 402 of FIG. 4A, or a portion thereof, apparatus 410 of FIG. 4B, or a portion thereof, apparatus 502 of FIGS. 5A-5B, or a portion thereof, apparatus 512 of FIGS. 5C-5D, or a portion thereof, apparatus 702 of FIG. 7A, or a portion thereof, apparatus 712 of FIG. 7B, or a portion thereof, apparatus 722 of FIG. 7C, or a portion thereof, apparatus 732 of FIG. 7D, or a portion thereof, apparatus 752 of FIG. 7E, or a portion thereof, or apparatus 762 of FIG. 7F, or a portion thereof, may utilize the set of operations. The apparatus may comprise means, including, for example processor 11 of FIG. 1, for performance of such operations. In an example embodiment, an apparatus, for example electronic apparatus 10 of FIG. 1, is transformed by having memory, for example memory 12 of FIG. 1, comprising computer code configured to, working with a processor, for example processor 11 of FIG. 1, cause the apparatus to perform set of operations of FIG. 8.

In some circumstances, a user of a separate apparatus may wish to perform an exercise routine simultaneously with a user of the apparatus. For example, the apparatus may modify the exercise routine presented to the user of the apparatus to maintain a similar pace with the user of the separate apparatus. In at least one example embodiment, the apparatus enters a collaborative exercise session with a separate apparatus. In at least one example embodiment, the collaborative exercise session is a mode of operation in which the apparatus is configured to influence a separate apparatus exercise plan, allow a separate apparatus to influence the exercise plan of the apparatus, and/or the like. A collaborative exercise session may refer to an interactive session in which a plurality of apparatuses communicate exercise information. In at least one example embodiment, exercise information refers to information that is indicative of at least part of an exercise plan. For example, the exercise information may comprise exercise route segment information, exercise instruction information, exercise pace information, exercise route segment information, exercise activity information, and/or the like. In at least one example embodiment, the apparatuses communicate exercise information over a communication channel, similar as described regarding FIG. 2. In circumstances such as these, the collaborative exercise session may aid the performance of such an exercise routine.

In at least one example embodiment the apparatus receives exercise information from a separate apparatus based, at least in part, on the collaborative exercise session. A collaborative exercise session may be a discrete session with a beginning and an end, such that sending and receiving of exercise information is confined to the duration of the collaborative exercise session. An apparatus may enter in a session by establishing the session, joining an already established session, and/or the like. In at least one example embodiment, the apparatus terminates the collaborative exercise session subsequent to the receipt of exercise information from the separate apparatus. Termination may comprise exit of the session, disestablishment of the session, and/or the like. In at least one example embodiment, the apparatus sends exercise information to the separate apparatus that comprises information indicative of the physiological state of the user. In at least one example embodiment, the apparatus sends exercise information to the separate apparatus that comprises information indicative of the exercise pace of the user.

At interaction 804, apparatus 800 establishes a collaborative exercise session with apparatus 802.

At interaction 806, apparatus 800 sends exercise information to apparatus 802, based, at least in part, on the establishment of the collaborative exercise session.

At interaction 808, apparatus 802 sends exercise information to apparatus 800, based, at least in part, on the establishment of the collaborative exercise session.

At interaction 810, apparatus 800 terminates the collaborative exercise session with apparatus 802.

Figure 9A:
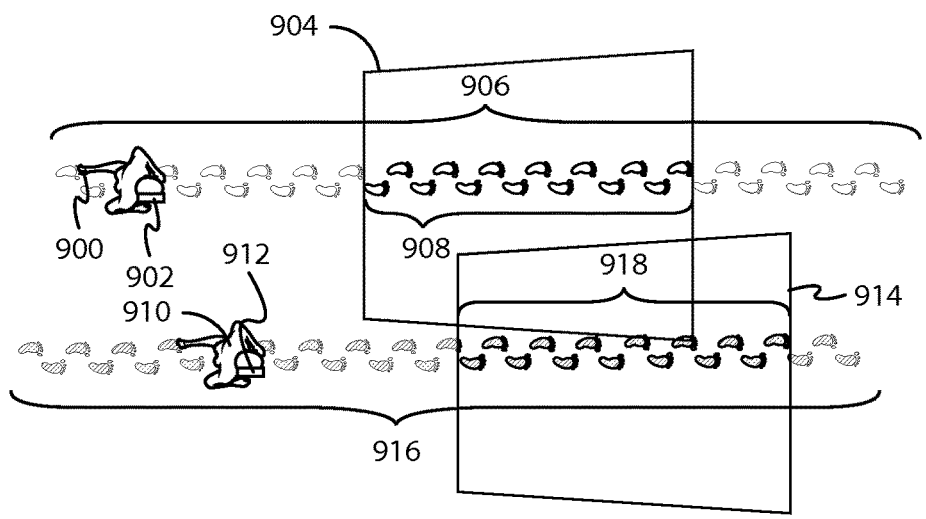
FIGS. 9A-9C are diagrams illustrating a collaborative exercise session according to at least one example embodiment.
Figure 9B:
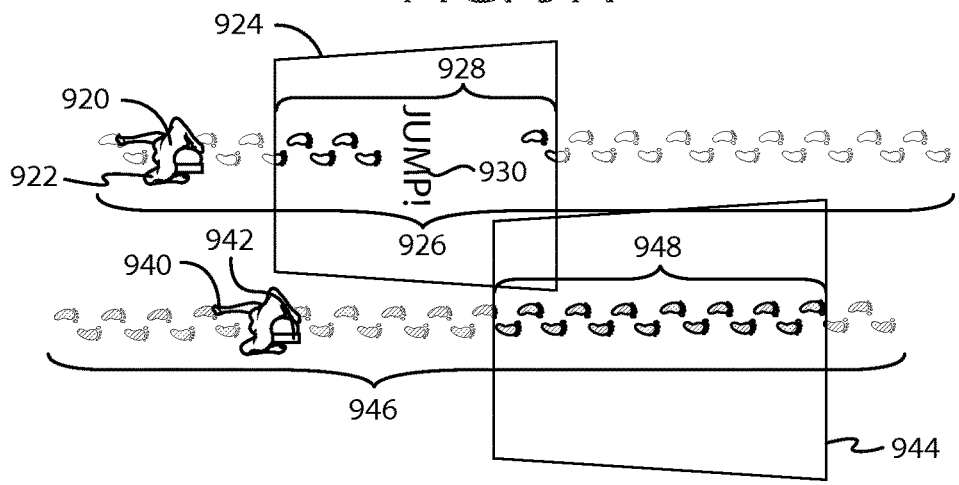
Figure 9C:
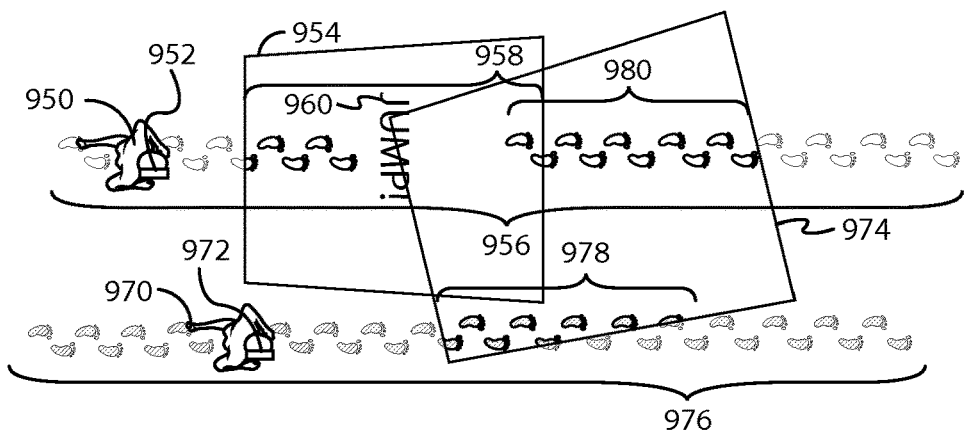

FIGS. 9A-9C are diagrams illustrating a collaborative exercise session according to at least one example embodiment. The examples of FIGS. 9A-9C are merely examples and do not limit the scope of the claims. For example, the number of apparatuses may vary, the type of apparatuses may vary, the type of exercise may vary, and/or the like.

As previously described, it may be desirable for an apparatus to enter a collaborative exercise session with a separate apparatus. For example, apparatus 902 of FIG. 9A may enter into a separate collaborative exercise session with apparatus 912 of FIG. 9A. In this manner, an apparatus may receive exercise information from the separate apparatus. For example, apparatus 902 may receive exercise information from apparatus 912. In circumstances such as these, it may be desirable for the exercise information to comprise information indicative of exercise pace of a user of the separate apparatus. For example, the apparatus may determine that the exercise pace of the user of the apparatus substantially exceeds the exercise pace of the user of the separate apparatus. Substantially exceeding an exercise pace may refer to exceeding a threshold value, exceeding a value designated by the user, the user of the separate apparatus being unable to maintain the exercise pace of the user of the apparatus, exceeding a pace by more than a particular percentage, and/or the like.

In some circumstances, it may be desirable for the exercise information to comprise information indicative of physiological information of a user of the separate apparatus substantially exceeding a threshold value. For example, the apparatus may modify the exercise plan such that the exercise plan is performed at a reduced pace and the reduced exercise pace is based, at least in part, on the physiological information of the user of the separate apparatus substantially exceeding a threshold value. The threshold value may be designated by exercise instruction information, medically predetermined, designated by a user, and/or the like.

FIG. 9A illustrates user 900 wearing apparatus 902 comprising a display. Apparatus 902 may comprise any type of display, such as a display similar as described regarding FIG. 3, FIGS. 4A-4B, and/or the like. In the example of FIG. 9A, apparatus 902 has a field of view of the display 904, and user 900 is performing an exercise activity related to exercise route segment 906. Even though exercise route segment is 906 is illustrated as a series of footprints, it should be understood that exercise route segment 906 may be represented with other symbols, text, graphics, and/or the like. In the example of FIG. 9A, apparatus 902 is causing display of exercise indicator 908 within field of view of the display 904. Even though exercise indicator 908 is illustrated as a series of footprints, it should be understood that exercise indicator 908 may be displayed as other symbols, text, graphics, and/or the like. It should be understood that exercise indicator 908 corresponds with a portion of exercise route segment 906. It can be seen that apparatus 902 is causing display of exercise indicator 908 in the field of view of the display 904 so that exercise indicator 908 is observable by the user.

Additionally, FIG. 9A illustrates user 910 wearing apparatus 912 comprising a display. Apparatus 912 may comprise any type of display, such as a display similar as described regarding FIG. 3, FIGS. 4A-4B, and/or the like. In the example of FIG. 9A, apparatus 912 has a field of view of the display 914, and user 910 is performing an exercise activity related to exercise route segment 916. Even though exercise route segment is 916 is illustrated as a series of footprints, it should be understood that exercise route segment 916 may be represented with other symbols, text, graphics, and/or the like. In the example of FIG. 9A, apparatus 912 is causing display of exercise indicator 918 within field of view of the display 914. Even though exercise indicator 918 is illustrated as a series of footprints, it should be understood that exercise indicator 918 may be displayed as other symbols, text, graphics, and/or the like. It should be understood that exercise indicator 918 corresponds a portion of exercise route segment 916. It can be seen that apparatus 912 is causing display of exercise indicator 918 in the field of view of the display 914 so that exercise indicator 918 is observable by the user.

As previously described, in many circumstances it may be desirable for an apparatus to modify an exercise plan. For example, it may be desirable to modify an exercise plan based on a collaborative exercise session. In at least one example embodiment, modification of an exercise plan comprises modification of exercise instruction information that is indicative of exercise pace such that corresponding exercise instruction information comprised by the modified exercise plan is indicative of at least one additional exercise activity. The additional exercise activity may be similar as described regarding FIGS. 7A-7F. For example, a user may be performing an exercise plan similar to exercise plan the exercise plan represented by exercise route segment 906 of FIG. 9A. In this example, an apparatus worn by the user may modify the exercise plan being performed, such that it conforms with an exercise plan similar to the exercise plan represented by exercise route segments 926 and 932 and additional exercise indicator 930 of FIG. 9B. Such a new exercise plan may have an exercise pace closer to the exercise pace being performed by the user of a separate apparatus.

As previously described, in some circumstances it may be desirable to modify an exercise plan. In circumstances such as these, it may be desirable for an apparatus to cause display of another exercise indicator that indicates exercise instruction information that corresponds with a portion of the modified exercise plan. For example, the apparatus may display additional exercise indicator 930 of FIG. 9B. In some circumstances, it may be desirable for an apparatus to determine a portion of a modified exercise plan, a portion of a modified exercise that corresponds with the location of the user, and/or the like. For example, the apparatus may limit display of information related to a modified exercise plan to a portion of the modified exercise plan near the current location of the user. An apparatus may determine a portion of a modified exercise plan that corresponds with a location of the user similar as described regarding FIG. 12.

As previously described, a collaborative exercise session may be used for a user of an apparatus and a user of a separate apparatus to maintain a similar exercise pace. In circumstances such as these, it may be desirable for the apparatus to modify an exercise plan to reflect a reduced pace from the exercise plan if a user of the apparatus is exercising at an exercise pace faster than an exercise pace of a user of a separate apparatus. For example, the modification of the exercise plan may comprise modification of exercise instruction information that is indicative of exercise pace such that corresponding exercise instruction information comprised by the modified exercise plan is indicative of a lesser exercise pace. In at least one example embodiment, the reduced exercise pace is based, at least in part, on the determination that the exercise pace of the user substantially exceeds the exercise pace of the user of the separate apparatus. In at least one example embodiment, the reduced exercise pace is based, at least in part, on the physiological information of the user of the separate apparatus substantially exceeding the threshold value.

In some circumstances, it may be desirable for the modification of the exercise plan to comprise modification of exercise instruction information that is indicative of exercise pace such that corresponding exercise instruction information comprised by the modified exercise plan is indicative of at least one replacement exercise activity. A replacement exercise activity may refer to an activity that is used to replace a previously designated activity within an exercise plan. For example, if a portion of an exercise plan, such as exercise instruction information 612 of FIG. 6A designated an exercise activity of running, a replacement activity may designate walking. In at least one example embodiment, the replacement exercise activity comprises at least one of walking, walking with a particular characteristic, running, running with a particular characteristic, jumping, hopping, bounding, bouncing, skipping and/or the like.

FIG. 9B illustrates user 920 wearing apparatus 922 comprising a display. Apparatus 922 may comprise any type of display, such as a display similar as described regarding FIG. 3, FIGS. 4A-4B, and/or the like. In the example of FIG. 9B, apparatus 922 has a field of view of the display 924, and user 920 is performing an exercise activity related to exercise route segment 926. Even though exercise route segment is 926 is illustrated as a series of footprints, it should be understood that exercise route segment 926 may be represented with other symbols, text, graphics, and/or the like. In the example of FIG. 9B, apparatus 922 is causing display of exercise indicator 928 within field of view of the display 924. Even though exercise indicator 928 is illustrated as a series of footprints and text, it should be understood that exercise indicator 928 may be displayed as other symbols, text, graphics, and/or the like. It should be understood that exercise indicator 928 corresponds with a portion of exercise route segment 926. It can be seen that apparatus 922 is causing display of exercise indicator 928 in the field of view of the display 9244 so that exercise indicator 928 is observable by the user. In the example of FIG. 9B, apparatus 922 is causing display of additional exercise indicator 930 within field of view of the display 924. Even though additional exercise indicator 930 is illustrated as text, it should be understood that additional exercise indicator 930 may be displayed as symbols, other text, graphics, and/or the like.

Additionally, FIG. 9B illustrates user 940 wearing apparatus 942 comprising a display. Apparatus 942 may be any type of display, such as a display similar as described regarding FIG. 3, FIGS. 4A-4B, and/or the like. In the example of FIG. 9B, apparatus 942 has a field of view of the display 944, and user 940 is performing an exercise activity related to exercise route segment 946. Even though exercise route segment is 946 is illustrated as a series of footprints, it should be understood that exercise route segment 946 may be represented with other symbols, text, graphics, and/or the like. In the example of FIG. 9B, apparatus 942 is causing display of exercise indicator 948 within field of view of the display 944. Even though exercise indicator 948 is illustrated as a series of footprints, it should be understood that exercise indicator 948 may be displayed as other symbols, text, graphics, and/or the like. It should be understood that exercise indicator 948 corresponds with a portion of exercise route segment 946. It can be seen that apparatus 942 is causing display of exercise indicator 948 in the field of view of the display 944 so that exercise indicator 948 is observable by the user.

In some circumstances, it may be desirable for an apparatus to display information indicative of an exercise plan being displayed by a separate apparatus. For example, in a collaborative exercise session, it may be desirable for a user of the apparatus to see the exercise plan being performed by a user of the separate apparatus. In this manner, the user may be able to modify the exercise pace during performance of their exercise routine to be similar to the exercise pace being performed by the user of the apparatus, anticipate any sudden changes in the user of the separate apparatus's exercise routine, and/or the like.

FIG. 9C illustrates user 950 wearing apparatus 952 comprising a display. Apparatus 952 may be comprise type of display, such as a display similar as described regarding FIG. 3, FIGS. 4A-4B, and/or the like. In the example of FIG. 9C, apparatus 952 has a field of view of the display 954, and user 950 is performing an exercise activity related to exercise route segment 956. Even though exercise route segment is 956 is illustrated as a series of footprints, it should be understood that exercise route segment 956 may be represented with other symbols, text, graphics, and/or the like. In the example of FIG. 9C, apparatus 952 is causing display of exercise indicator 958 within field of view of the display 954. Even though exercise indicator 958 is illustrated as a series of footprints and text, it should be understood that exercise indicator 958 may be displayed as other symbols, text, graphics, and/or the like. It should be understood that exercise indicator 958 corresponds with a portion of exercise route segment 956. It can be seen that apparatus 952 is causing display of exercise indicator 958 in the field of view of the display 954 so that exercise indicator 958 is observable by the user. In the example of FIG. 9C, apparatus 952 is causing display of additional exercise indicator 960 within field of view of the display 954. Even though additional exercise indicator 960 is illustrated as text, it should be understood that additional exercise indicator 960 may be displayed as symbols, other text, graphics, and/or the like.

Additionally, FIG. 9C illustrates user 970 wearing apparatus 972 comprising a display. Apparatus 972 may comprise any type of display, such as a display similar as described regarding FIG. 3, FIGS. 4A-4B, and/or the like. In the example of FIG. 9C, apparatus 972 has a field of view of the display 974, and user 970 is performing an exercise activity related to exercise route segment 976. Even though exercise route segment is 976 is illustrated as a series of footprints, it should be understood that exercise route segment 976 may be represented with other symbols, text, graphics, and/or the like. In the example of FIG. 9C, apparatus 972 is causing display of exercise indicator 978 within field of view of the display 974. Even though exercise indicator 978 is illustrated as a series of footprints, it should be understood that exercise indicator 978 may be displayed as other symbols, text, graphics, and/or the like. It should be understood that exercise indicator 978 corresponds with a portion of exercise route segment 976. It can be seen that apparatus 972 is causing display of exercise indicator 978 in the field of view of the display 974 so that exercise indicator 978 is observable by the user. In the example of FIG. 9C, apparatus 972 is causing display of exercise indicator 980 within field of view of the display 974. Even though exercise indicator 980 is illustrated as a series of footprints, it should be understood that exercise indicator 980 may be displayed as other symbols, text, graphics, and/or the like. It should be understood that exercise indicator 980 corresponds with a portion of exercise route segment 962. It can be seen that apparatus 972 is causing display of exercise indicator 980 in the field of view of the display 974 so that exercise indicator 980 is observable by the user. As can be seen in the example of FIG. 9C, user 970 may look toward the path of user 950 and perceive information that allows user 970 to determine a portion of user 950's exercise plan.

Figure 10A:
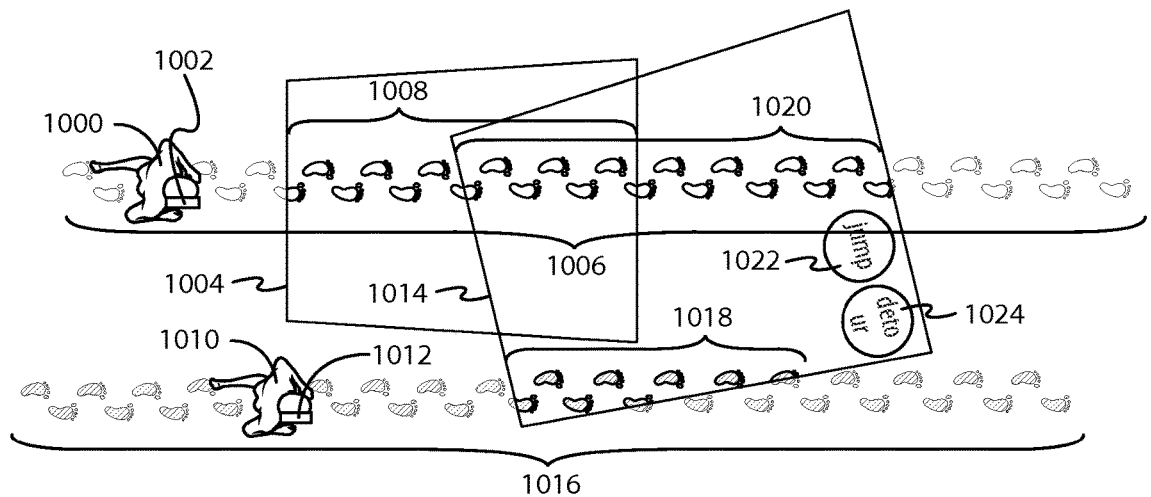
FIGS. 10A-10B are diagrams illustrating selection of an exercise instruction directive candidate according to at least one example embodiment.
Figure 10B:
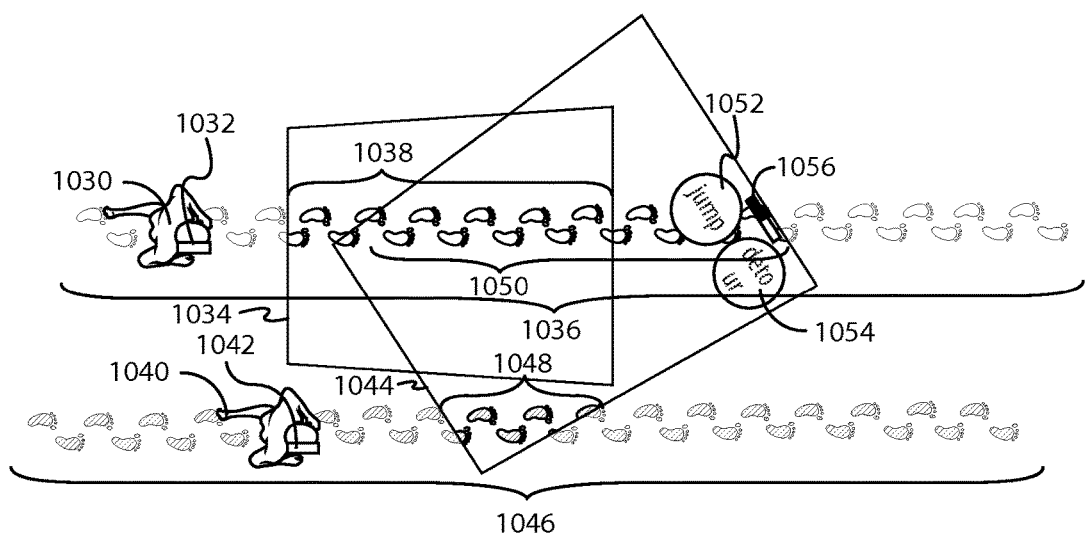

FIGS. 10A-10B are diagrams illustrating selection of an exercise instruction directive candidate according to at least one example embodiment. The examples of FIGS. 10A-10B are merely examples and do not limit the scope of the claims. For example, the apparatus may vary, the exercise instruction directive candidates may vary, the number of exercise instruction directive candidates may vary, and/or the like.

In some circumstances, it may be desirable for an apparatus to designate the occurrence of an achievement. Occurrence of an achievement may refer to a user meeting a predetermined condition, exceeding a threshold, performing a predetermined goal, and/or the like. For example, a collaborative exercise session between an apparatus and a separate apparatus may comprise a game like component. For instance, a user may score points for occurrence of an achievement, occurrence of an achievement may trigger an interaction with the separate apparatus, send an exercise instruction directive to the separate apparatus, and/or the like. An exercise instruction directive may refer to an instruction for an apparatus to modify an exercise plan, display an alternate exercise activity, and/or the like. In at least one example embodiment, an apparatus sends exercise information comprising an exercise instruction directive based, at least in part, on determination that an achievement has occurred.

Designation of an achievement may be based, at least in part, on exercise information. For example, if a user of an apparatus substantially exceeds the exercise pace of a user of a separate apparatus, the apparatus may designate an occurrence of an achievement. In another example, designating an occurrence of an achievement may be based, at least in part, on a determination that the physiological state of the user of the apparatus substantially exceeds another physiological state of the user designated by exercise instruction information, that the user has completed a particular exercise route segment with a quicker time than another user, completes at least a portion of an exercise route segment with an average heart rate below a predetermined heart rate, and/or the like.

In some circumstances, it may be desirable for an apparatus to display an exercise instruction directive candidate. For example, when an apparatus is in a collaborative exercise session with a separate apparatus, a user of the apparatus may select a displayed exercise instruction directive candidate to cause sending of an exercise instruction directive to the separate apparatus. For instance, if the collaborative exercise session comprises game like elements, the user of the apparatus may be able to "motivate" the user of the separate apparatus by selecting an exercise instruction directive candidate displayed in response to occurrence of an achievement. In at least one example embodiment, the apparatus identifies one or more exercise instruction directive candidates based, at least in part, on occurrence of an achievement. In at least one example embodiment, the apparatus receives information indicative of selection of an exercise instruction directive candidate. In a least one example embodiment, an exercise instruction directive corresponds with an exercise instruction directive candidate. In at least one example embodiment, modification of an exercise plan is performed in conformance with an exercise instruction directive. For example, upon occurrence of an achievement, an apparatus may receive an exercise instruction directive from a separate apparatus. The exercise instruction directive may instruct the apparatus to modify an exercise plan with an additional exercise activity as "motivation" for occurrence of the achievement. For example, the exercise instruction directive may instruct the apparatus to add jumping to the exercise plan, add running with a certain characteristic to the exercise plan, and/or the like. In this manner, the user may have to exert more energy to maintain an exercise pace, to catch up with a user of a separate apparatus, and/or the like. Such "motivation" may inspire the user of the apparatus to exercise beyond their normal abilities, to maintain the exercise pace of an exercise partner, and/or the like.

FIG. 10A illustrates user 1000 wearing apparatus 1002 comprising a display. Apparatus 1002 may comprise any type of display, such as a display similar as described regarding FIG. 3, FIGS. 4A-4B, and/or the like. In the example of FIG. 10A, apparatus 1002 has a field of view of the display 1004, and user 1000 is performing an exercise activity related to exercise route segment 1006. Even though exercise route segment is 1006 is illustrated as a series of footprints, it should be understood that exercise route segment 1006 may be represented with other symbols, text, graphics, and/or the like. In the example of FIG. 10A, apparatus 1002 is causing display of exercise indicator 1008 within field of view of the display 1004. Even though exercise indicator 1008 is illustrated as a series of footprints and text, it should be understood that exercise indicator 1008 may be displayed as other symbols, text, graphics, and/or the like. It should be understood that exercise indicator 1008 corresponds with a portion of exercise route segment 1006. It can be seen that apparatus 1002 is causing display of exercise indicator 1008 in the field of view of the display 1004 so that exercise indicator 1008 is observable by the user.

Additionally, FIG. 10A illustrates user 1010 wearing apparatus 1012 comprising a display. Apparatus 1012 may comprise any type of display, such as a display similar as described regarding FIG. 3, FIGS. 4A-4B, and/or the like. In the example of FIG. 10A, apparatus 1012 has a field of view of the display 1014, and user 1010 is performing an exercise activity related to exercise route segment 1016. Even though exercise route segment is 1016 is illustrated as a series of footprints, it should be understood that exercise route segment 1016 may be represented with other symbols, text, graphics, and/or the like. In the example of FIG. 10A, apparatus 1012 is causing display of exercise indicator 1018 within field of view of the display 1014. Even though exercise indicator 1018 is illustrated as a series of footprints, it should be understood that exercise indicator 1018 may be displayed as other symbols, text, graphics, and/or the like. It should be understood that exercise indicator 1018 corresponds with a portion of exercise route segment 1016. It can be seen that apparatus 1012 is causing display of exercise indicator 1018 in the field of view of the display 1014 so that exercise indicator 1018 is observable by the user. In the example of FIG. 10A, apparatus 1012 is causing display of exercise indicator 1020 within field of view of the display 1014. Even though exercise indicator 1020 is illustrated as a series of footprints, it should be understood that exercise indicator 1020 may be displayed as other symbols, text, graphics, and/or the like. It should be understood that exercise indicator 1020 corresponds with a portion of exercise route segment 1006. It can be seen that apparatus 1012 is causing display of exercise indicator 1020 in the field of view of the display 1014 so that exercise indicator 1018 is observable by the user.

In the example of FIG. 10A, apparatus 1012 is causing display of exercise instruction directive candidates 1022 and 1024 within field of view of the display 1014. Even though exercise instruction directive candidates 1022 and 1024 are illustrated as a shapes with text, it should be understood that exercise instruction directive candidates 1022 and 1024 may be displayed as other shapes, symbols, text, graphics, and/or the like.

FIG. 10B illustrates user 1030 wearing apparatus 1032 comprising a display. Apparatus 1032 may comprise any type of display, such as a display similar as described regarding FIG. 3, FIGS. 4A-4B, and/or the like. In the example of FIG. 10B, apparatus 1032 has a field of view of the display 1034, and user 1030 is performing an exercise activity related to exercise route segment 1036. Even though exercise route segment is 1036 is illustrated as a series of footprints, it should be understood that exercise route segment 1036 may be represented with other symbols, text, graphics, and/or the like. In the example of FIG. 10B, apparatus 1032 is causing display of exercise indicator 1038 within field of view of the display 1034. Even though exercise indicator 1038 is illustrated as a series of footprints and text, it should be understood that exercise indicator 1038 may be displayed as other symbols, text, graphics, and/or the like. It should be understood that exercise indicator 1038 corresponds with a portion of exercise route segment 1036. It can be seen that apparatus 1032 is causing display of exercise indicator 1038 in the field of view of the display 1034 so that exercise indicator 1038 is observable by the user.

Additionally, FIG. 10B illustrates user 1040 wearing apparatus 1042 comprising a display. Apparatus 1042 may comprise any type of display, such as a display similar as described regarding FIG. 3, FIGS. 4A-4B, and/or the like. In the example of FIG. 10B, apparatus 1042 has a field of view of the display 1044, and user 1040 is performing an exercise activity related to exercise route segment 1046. Even though exercise route segment is 1046 is illustrated as a series of footprints, it should be understood that exercise route segment 1046 may be represented with other symbols, text, graphics, and/or the like. In the example of FIG. 10B, apparatus 1042 is causing display of exercise indicator 1048 within field of view of the display 1044. Even though exercise indicator 1048 is illustrated as a series of footprints, it should be understood that exercise indicator 1048 may be displayed as other symbols, text, graphics, and/or the like. It should be understood that exercise indicator 1048 corresponds with a portion of exercise route segment 1046. It can be seen that apparatus 1042 is causing display of exercise indicator 1048 in the field of view of the display 1044 so that exercise indicator 1048 is observable by the user. In the example of FIG. 10B, apparatus 1042 is causing display of exercise indicator 1050 within field of view of the display 1044. Even though exercise indicator 1050 is illustrated as a series of footprints, it should be understood that exercise indicator 1050 may be displayed as other symbols, text, graphics, and/or the like. It should be understood that exercise indicator 1050 corresponds with a portion of exercise route segment 1036. It can be seen that apparatus 1042 is causing display of exercise indicator 1050 in the field of view of the display 1044 so that exercise indicator 1050 is observable by the user.

In the example of FIG. 10B, apparatus 1042 is causing display of exercise instruction directive candidates 1052 and 1054 within field of view of the display 1044. Even though exercise instruction directive candidates 1052 and 1054 are illustrated as a shapes with text, it should be understood that exercise instruction directive candidates 1052 and 1054 may be displayed as other shapes, symbols, text, graphics, and/or the like. The example of FIG. 10B illustrates exercise instruction directive candidate selection indicator 1056.

In some circumstances, the orientation of the apparatus may cause the field of view of a display comprised by the apparatus to display an exercise instruction directive candidate in alignment with an exercise route segment of the separate apparatus. In circumstances such as these, it may be desirable for the apparatus to determine that, the exercise instruction directive candidate has become aligned with an exercise route segment of the separate apparatus. For example, the apparatus may present additional information, options, alerts, and/or the like to the user based, at least in part, on the determination that the exercise instruction directive candidate has become aligned with an exercise route segment of the separate apparatus by way of apparatus orientation information associated with the apparatus. In at least one example embodiment, the apparatus determines that the exercise instruction directive candidate has become aligned with an exercise route segment of the separate apparatus by way of apparatus orientation information associated with the apparatus. For example, the apparatus may determine that that the exercise instruction directive candidate has become aligned with an exercise route segment of the separate apparatus from apparatus orientation information received from a global positioning system sensor, radio triangulation, a magnetometer sensor, a gyroscope sensor, an accelerometer sensor, an optical sensor, an imaging sensor, and/or the like. For instance, the apparatus may compare heading information received from a GPS sensor with orientation information received from a gyroscope sensor to determine that the exercise instruction directive candidate has become aligned with an exercise route segment of the separate apparatus. In at least one example embodiment, the apparatus determines that the exercise instruction directive candidate has become aligned with an exercise route segment of the separate apparatus by way of information received from a camera module. For example, the apparatus may comprise a camera module configured with a field of view that corresponds with a field of view of the display of the apparatus. The apparatus may receive information from the camera module indicating that the exercise instruction directive candidate has become aligned with an exercise route segment of the separate apparatus. For instance, if the separate apparatus displays a projected image of an exercise route segment, the camera module may capture an image comprising the projected exercise route segment. In this manner, the apparatus may determine that the information received from the camera module is indicative that the exercise instruction directive candidate has become aligned with an exercise route segment of the separate apparatus. In the example of FIG. 10B, it can be seen that exercise instruction directive candidates 1052 is in alignment with exercise route segment 1036 based, at least in part, on the superimposed display of exercise instruction directive 1052 above exercise indicator 1050. In circumstances such as these, apparatus 1042 may determine that an exercise instruction directive candidate has been selected by user 1040. For example, apparatus 1042 may determine the user 1042 has selected exercise instruction directive candidate 1052 based, at least in part on exercise instruction directive candidate 1052 being aligned with exercise route segment 1036. It may be desirable for an apparatus to display an indicator that indicates that an exercise instruction directive candidate had become aligned with an exercise route segment of the separate apparatus. For example, such an indicator may alert a user of the apparatus to the alignment. For instance, exercise instruction directive candidate selection indicator 1056 may alert user 1040 that exercise instruction directive candidate 1054 is in alignment with exercise route segment 1036 and has been selected.

Figure 11:
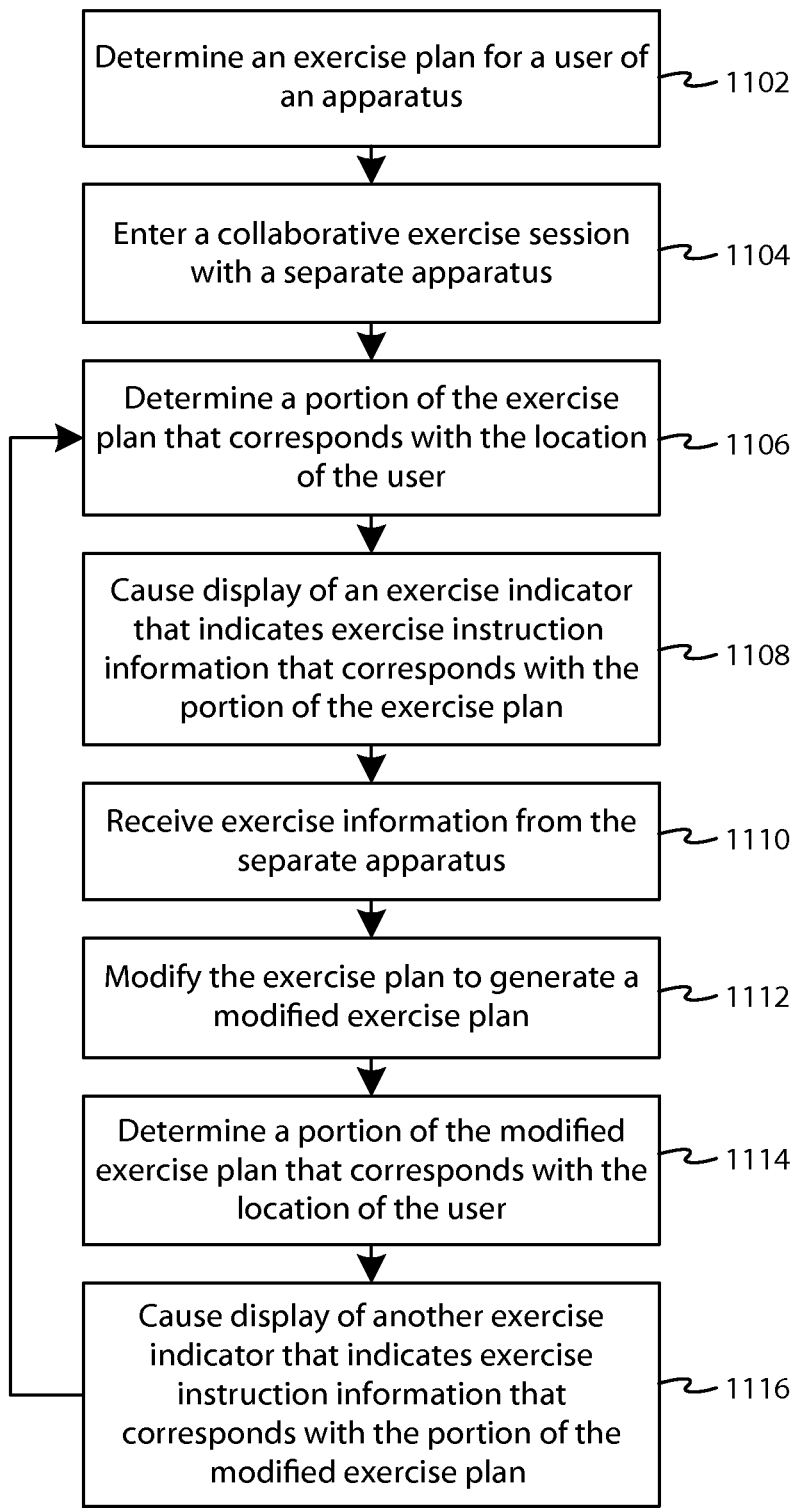
FIG. 11 is a flow diagram illustrating activities associated with modification of an exercise plan according to at least one example embodiment.

FIG. 11 is a flow diagram illustrating activities associated with modification of an exercise plan according to at least one example embodiment. In at least one example embodiment, there is a set of operations that corresponds with the activities of FIG. 11. An apparatus, for example electronic apparatus 10 of FIG. 1, or a portion thereof, may utilize the set of operations. The apparatus may comprise means, including, for example processor 11 of FIG. 1, for performance of such operations. In an example embodiment, an apparatus, for example electronic apparatus 10 of FIG. 1, is transformed by having memory, for example memory 12 of FIG. 1, comprising computer code configured to, working with a processor, for example processor 11 of FIG. 1, cause the apparatus to perform set of operations of FIG. 11.

At block 1102, the apparatus determines an exercise plan for a user of the apparatus. The exercise plan may correlate exercise instruction information with location information. The apparatus, the determination, and the exercise plan may be similar as described regarding FIG. 1, FIG. 2, FIG. 3, FIGS. 4A-4B, FIGS. 6A-6D, and FIGS. 7A-7D, FIGS. 9A-9C and FIGS. 10A-10B.

At block 1104, the apparatus enters a collaborative exercise session with a separate apparatus. The entering, the collaborative exercise session, and the separate apparatus may be similar as described regarding FIG. 1, FIG. 2, FIG. 3, FIG. 8, FIGS. 9A-9C, and FIGS. 10A-10B.

At block 1106, the apparatus determines a portion of the exercise plan that corresponds with a location of the user. The determination and the location may be similar as described regarding FIGS. 4A-4B, FIGS. 6A-6D, FIGS. 7A-7D, FIGS. 9A-9C and FIGS. 10A-10B.

At block 1108, the apparatus causes display of an exercise indicator that indicates exercise instruction information that corresponds with the portion of the exercise plan. The display, the exercise indicator, and the exercise instruction information may be similar as described regarding FIGS. 6A-6D, FIGS. 7A-7D, FIGS. 9A-9C, and FIGS. 10A-10B.

At block 1110, the apparatus receives exercise information from the separate apparatus. In this manner, the receipt of exercise information from the separate apparatus may be based, at least in part, on the collaborative exercise session. The receipt and the exercise information may be similar as described regarding FIGS. 6A-6D, FIG. 8, FIGS. 9A-9C, and FIGS. 10A-10B.

At block 1112, the apparatus modifies the exercise plan to generate a modified exercise plan. In this manner, the modification of the exercise plan may be based, at least in part, on the exercise information received from the separate apparatus. The modification, the generation, and the modified exercise plan may be similar as described regarding FIGS. 6A-6D, FIGS. 7A-7D, FIGS. 9A-9C, and FIGS. 10A-10B.

At block 1114, the apparatus determines a portion of the modified exercise plan that corresponds with a location of the user. The determination and the location of the user may be similar as described regarding FIGS. 6A-6D, FIGS. 7A-7D, FIGS. 9A-9C, and FIGS. 10A-10B.

At block 1116, the apparatus causes display of another exercise indicator that indicates exercise instruction information that corresponds with the portion of the modified exercise plan. The display, other exercise indicator, and the exercise instruction information may be similar as described regarding FIGS. 6A-6D, FIGS. 7A-7D, FIGS. 9A-9C, and FIGS. 10A-10B.

Figure 12:
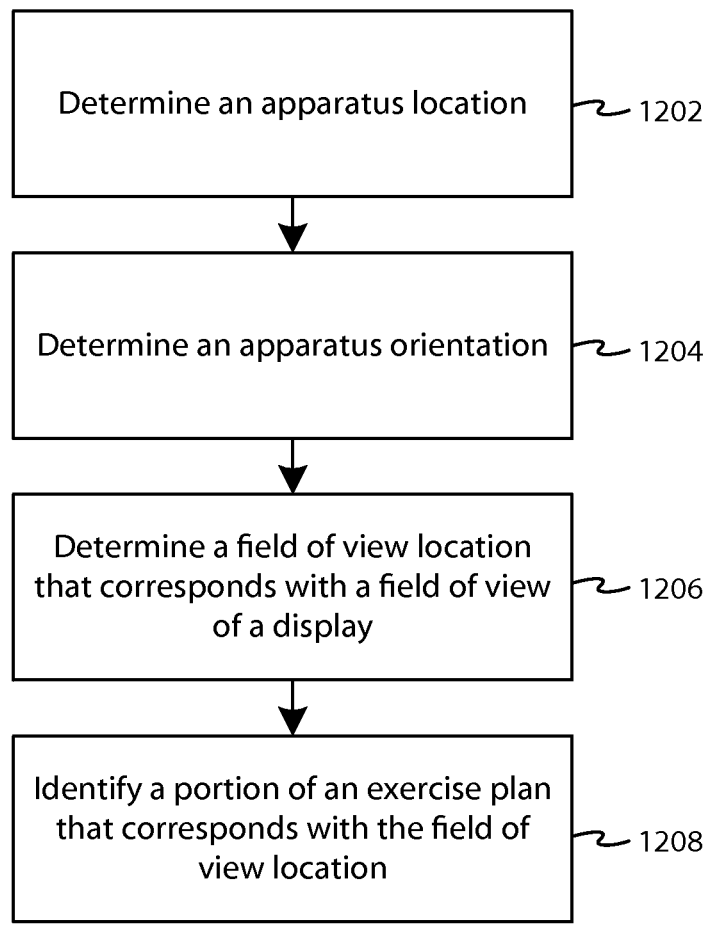
FIG. 12 is a flow diagram illustrating activities associated with identifying a portion of an exercise plan according to at least one example embodiment.

FIG. 12 is a flow diagram illustrating activities associated with identifying a portion of an exercise plan according to at least one example embodiment. In at least one example embodiment, there is a set of operations that corresponds with the activities of FIG. 12. An apparatus, for example electronic apparatus 10 of FIG. 1, or a portion thereof, may utilize the set of operations. The apparatus may comprise means, including, for example processor 11 of FIG. 1, for performance of such operations. In an example embodiment, an apparatus, for example electronic apparatus 10 of FIG. 1, is transformed by having memory, for example memory 12 of FIG. 1, comprising computer code configured to, working with a processor, for example processor 11 of FIG. 1, cause the apparatus to perform set of operations of FIG. 12.

As previously described, it may be desirable to determine a portion of an exercise plan, a portion of a modified exercise plan, and/or the like. Determination of a portion of a modified exercise plan may be similar to determination of a portion of an exercise plan.

At block 1202, the apparatus determines an apparatus location. The determination may be based, at least in part, on location sensor information. The apparatus, the determination, the location, location, and the location sensor information may be similar as described regarding FIGS. 5A-5D.

At block 1204, the apparatus determines an apparatus orientation. The determination may be based, at least in part, on orientation sensor information. The determination, the orientation, and the orientation sensor information may be similar as described regarding FIGS. 5A-5D.

At block 1206, the apparatus determines a field of view location that corresponds with a field of view of a display. The determination may be based, at least in part, on the apparatus location and the apparatus orientation. The determination, the field of view location, and the field of view of the display may be similar s described regarding FIGS. 5A-5D, FIGS. 7A-7F, FIGS. 9A-9C and FIGS. 10A-10B.

At block 1208, the apparatus identifies the portion of the exercise plan that corresponds with the field of view location. The identification and the exercise plan may be similar as described regarding FIGS. 6A-6C, FIGS. 7A-7F, FIGS. 9A-9C, and FIGS. 10A-10B.

Figure 13:
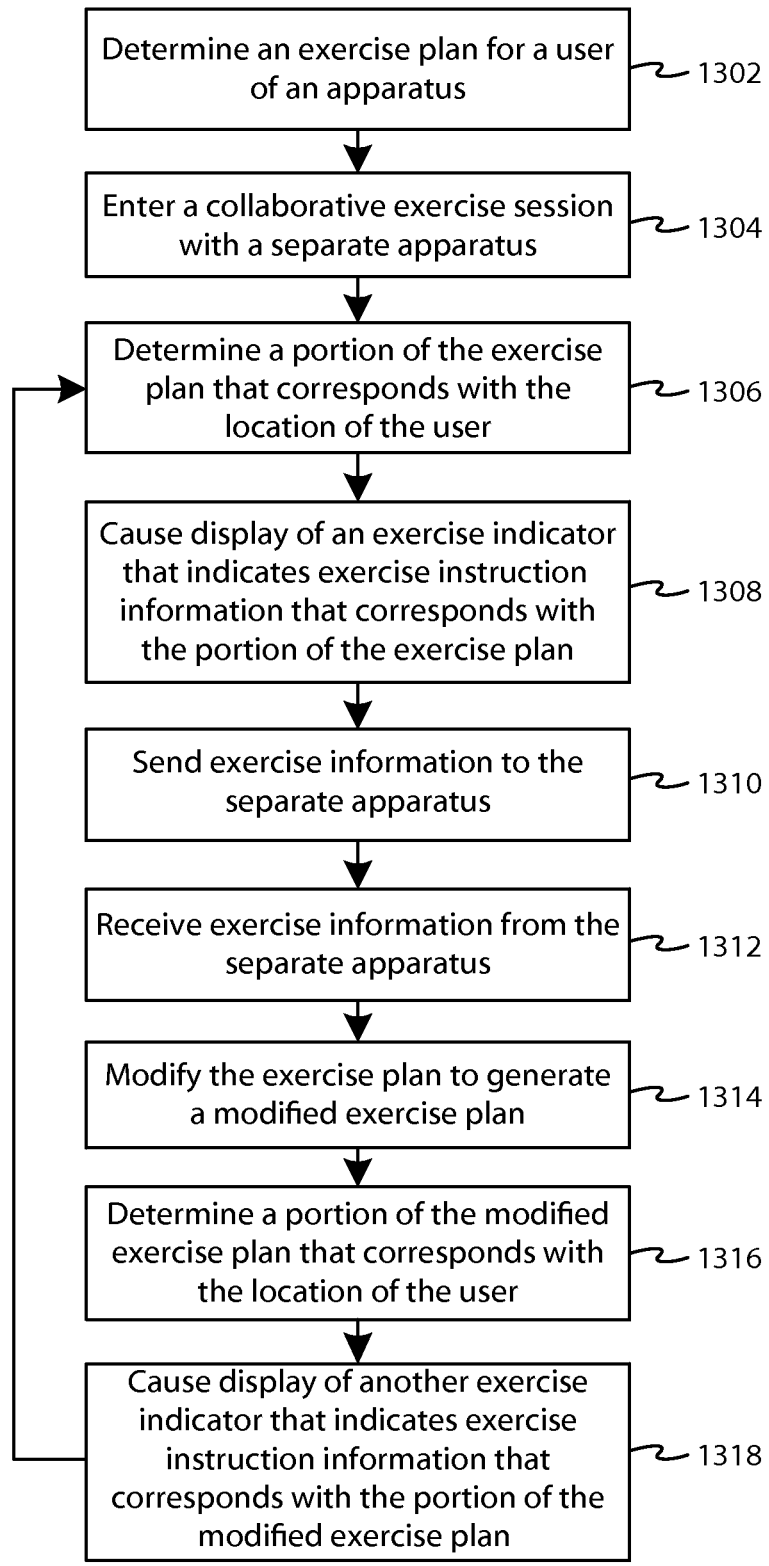
FIG. 13 is a flow diagram illustrating activities associated with sending exercise information to a separate apparatus according to at least one example embodiment.

FIG. 13 is a flow diagram illustrating activities associated with sending exercise information to a separate apparatus according to at least one example embodiment. In at least one example embodiment, there is a set of operations that corresponds with the activities of FIG. 13. An apparatus, for example electronic apparatus 10 of FIG. 1, or a portion thereof, may utilize the set of operations. The apparatus may comprise means, including, for example processor 11 of FIG. 1, for performance of such operations. In an example embodiment, an apparatus, for example electronic apparatus 10 of FIG. 1, is transformed by having memory, for example memory 12 of FIG. 1, comprising computer code configured to, working with a processor, for example processor 11 of FIG. 1, cause the apparatus to perform set of operations of FIG. 13.

As previously described, it may be desirable to send exercise information to a separate apparatus.

At block 1302, the apparatus determines an exercise plan for a user of the apparatus, similarly as described regarding block 1102 of FIG. 11. At block 1304, the apparatus enters a collaborative exercise session with a separate apparatus, similarly as described regarding block 1104 of FIG. 11. At block 1306, the apparatus determines a portion of the exercise plan that corresponds with a location of the user, similarly as described regarding block 1106 of FIG. 11. At block 1308, the apparatus causes display of an exercise indicator that indicates exercise instruction information that corresponds with the portion of the exercise plan, similarly as described regarding block 1108 of FIG. 11.

At block 1310, the apparatus sends exercise information to the separate apparatus. The sending and the exercise information may be similar as described regarding FIGS. 6A-6D, FIG. 8, FIGS. 9A-9C, and FIGS. 10A-10B.

At block 1312, the apparatus receives exercise information from the separate apparatus, similarly as described regarding block 1110 of FIG. 11. At block 1314, the apparatus modifies the exercise plan to generate a modified exercise plan, similarly as described regarding block 1112 of FIG. 11. At block 1316, the apparatus determines a portion of the modified exercise plan that corresponds with a location of the user, similarly as described regarding block 1114 of FIG. 11. At block 1318, the apparatus causes display of another exercise indicator that indicates exercise instruction information that corresponds with the portion of the modified exercise plan, similarly as described regarding block 1116 of FIG. 11.

Figure 14:
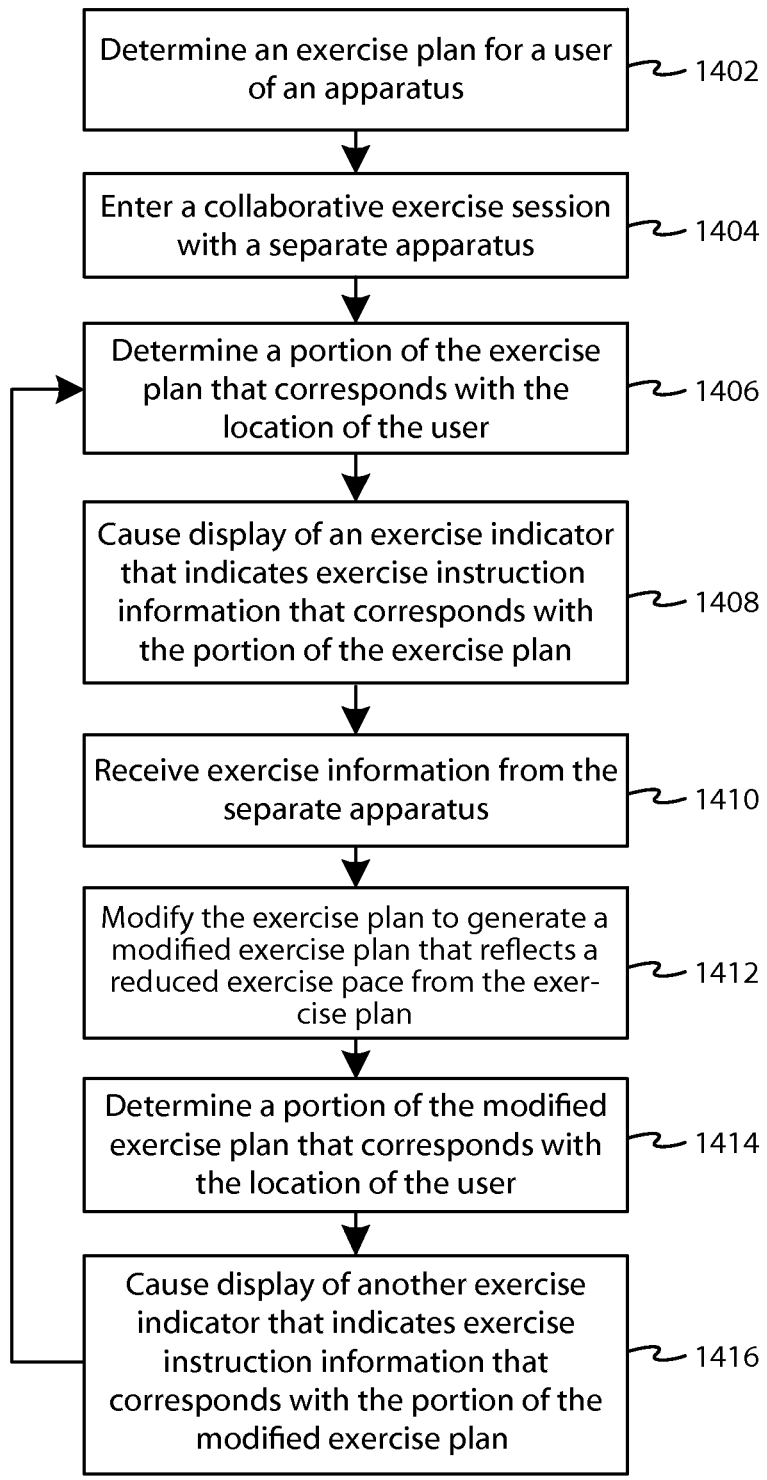
FIG. 14 is a flow diagram illustrating activities associated with modification of an exercise plan according to at least one example embodiment.

FIG. 14 is a flow diagram illustrating activities associated with modification of an exercise plan according to at least one example embodiment. In at least one example embodiment, there is a set of operations that corresponds with the activities of FIG. 14. An apparatus, for example electronic apparatus 10 of FIG. 1, or a portion thereof, may utilize the set of operations. The apparatus may comprise means, including, for example processor 11 of FIG. 1, for performance of such operations. In an example embodiment, an apparatus, for example electronic apparatus 10 of FIG. 1, is transformed by having memory, for example memory 12 of FIG. 1, comprising computer code configured to, working with a processor, for example processor 11 of FIG. 1, cause the apparatus to perform set of operations of FIG. 14.

As previously described, it may be desirable to modify an exercise plan to reflect a reduced exercise pace.

At block 1402, the apparatus determines an exercise plan for a user of the apparatus, similarly as described regarding block 1102 of FIG. 11. At block 1404, the apparatus enters a collaborative exercise session with a separate apparatus, similarly as described regarding block 1104 of FIG. 11. At block 1406, the apparatus determines a portion of the exercise plan that corresponds with a location of the user, similarly as described regarding block 1106 of FIG. 11. At block 1408, the apparatus causes display of an exercise indicator that indicates exercise instruction information that corresponds with the portion of the exercise plan, similarly as described regarding block 1108 of FIG. 11. At block 1410, the apparatus receives exercise information from the separate apparatus, similarly as described regarding block 1110 of FIG. 11.

At block 1412, the apparatus modifies the exercise plan to generate a modified exercise plan. In this manner, the modification of the exercise plan may be based, at least in part, on the exercise information received from the separate apparatus. The modification of the exercise plan may be performed such that the modified exercise plan reflects a reduced exercise pace from the exercise plan.

In this manner, the modification of the exercise plan may be based, at least in part, on the exercise information received from the separate apparatus. The modification, the generation, and the modified exercise plan may be similar as described regarding FIGS. 6A-6D, FIGS. 7A-7D, FIGS. 9A-9C, and FIGS. 10A-10B.

At block 1414, the apparatus determines a portion of the modified exercise plan that corresponds with a location of the user, similarly as described regarding block 1114 of FIG. 11. At block 1416, the apparatus causes display of another exercise indicator that indicates exercise instruction information that corresponds with the portion of the modified exercise plan, similarly as described regarding block 1116 of FIG. 11.

Figure 15:
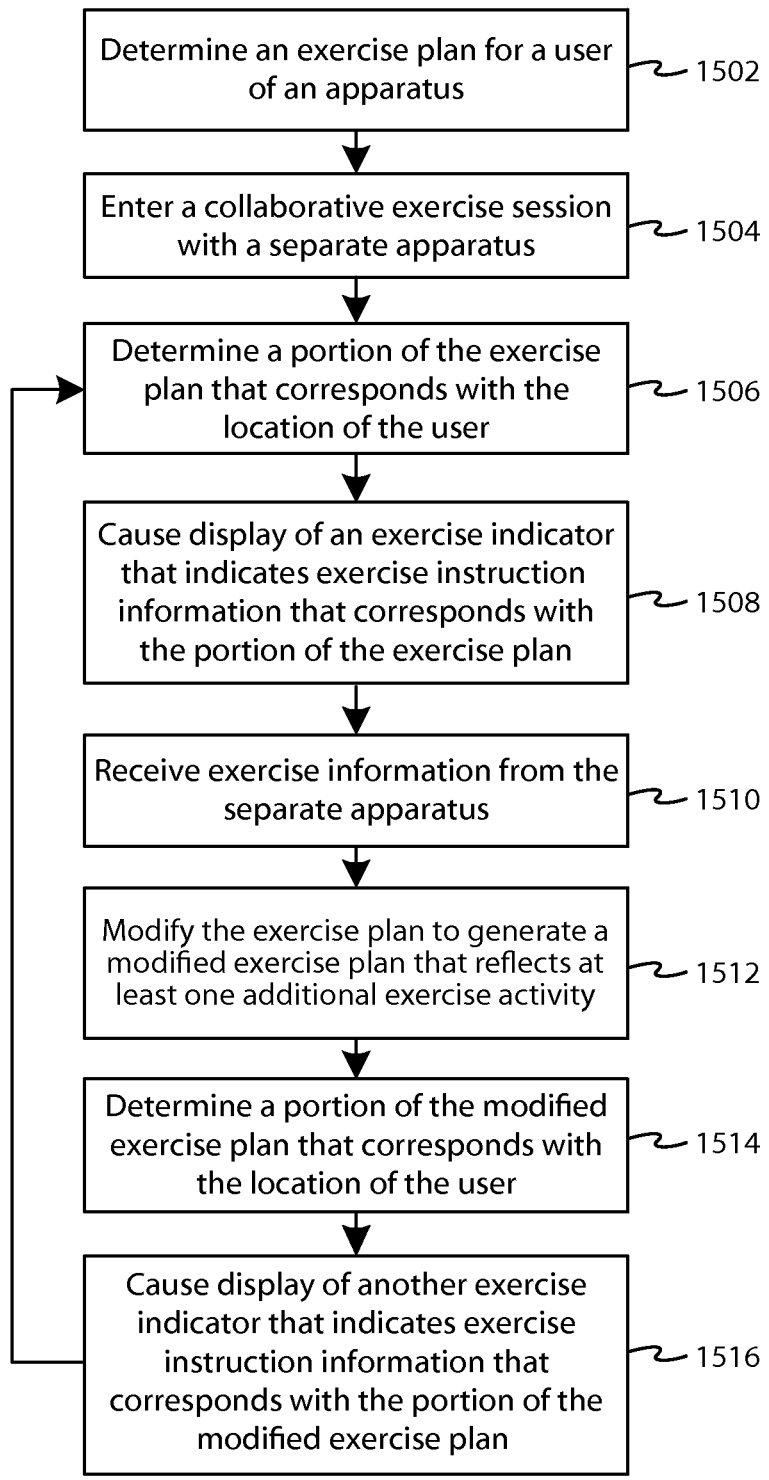
FIG. 15 is a flow diagram illustrating activities associated with modification of an exercise plan according to at least one example embodiment.

FIG. 15 is a flow diagram illustrating activities associated with modification of an exercise plan according to at least one example embodiment. In at least one example embodiment, there is a set of operations that corresponds with the activities of FIG. 15. An apparatus, for example electronic apparatus 10 of FIG. 1, or a portion thereof, may utilize the set of operations. The apparatus may comprise means, including, for example processor 11 of FIG. 1, for performance of such operations. In an example embodiment, an apparatus, for example electronic apparatus 10 of FIG. 1, is transformed by having memory, for example memory 12 of FIG. 1, comprising computer code configured to, working with a processor, for example processor 11 of FIG. 1, cause the apparatus to perform set of operations of FIG. 15.

As previously described, it may be desirable to modify an exercise plan to reflect at least one additional exercise activity.

At block 1502, the apparatus determines an exercise plan for a user of the apparatus, similarly as described regarding block 1102 of FIG. 11. At block 1504, the apparatus enters a collaborative exercise session with a separate apparatus, similarly as described regarding block 1104 of FIG. 11. At block 1506, the apparatus determines a portion of the exercise plan that corresponds with a location of the user, similarly as described regarding block 1106 of FIG. 11. At block 1508, the apparatus causes display of an exercise indicator that indicates exercise instruction information that corresponds with the portion of the exercise plan, similarly as described regarding block 1108 of FIG. 11. At block 1510, the apparatus receives exercise information from the separate apparatus, similarly as described regarding block 1110 of FIG. 11.

At block 1512, the apparatus modifies the exercise plan to generate a modified exercise plan. In this manner, the modification of the exercise plan may be based, at least in part, on the exercise information received from the separate apparatus. The modification of the exercise plan comprises modification of exercise instruction information that is indicative of exercise pace such that corresponding exercise instruction information comprised by the modified exercise plan is indicative of at least one additional exercise activity. In this manner, the modified exercise plan may reflect at least one additional exercise activity.

At block 1514, the apparatus determines a portion of the modified exercise plan that corresponds with a location of the user, similarly as described regarding block 1114 of FIG. 11. At block 1516, the apparatus causes display of another exercise indicator that indicates exercise instruction information that corresponds with the portion of the modified exercise plan, similarly as described regarding block 1116 of FIG. 11.

Figure 16:
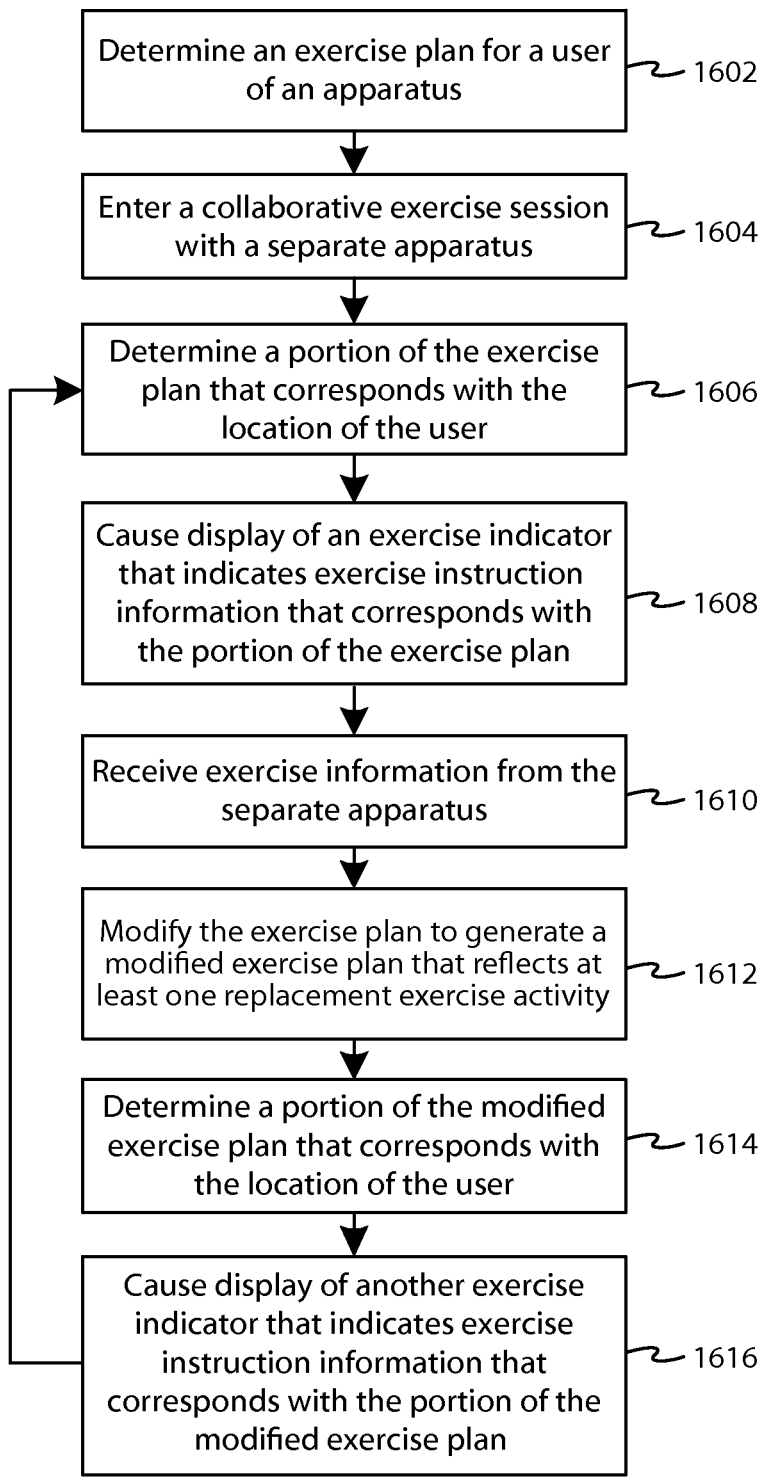
FIG. 16 is a flow diagram illustrating activities associated with determining an achievement has occurred according to at least one example embodiment.

FIG. 16 is a flow diagram illustrating activities associated with determining an achievement has occurred according to at least one example embodiment. In at least one example embodiment, there is a set of operations that corresponds with the activities of FIG. 16. An apparatus, for example electronic apparatus 10 of FIG. 1, or a portion thereof, may utilize the set of operations. The apparatus may comprise means, including, for example processor 11 of FIG. 1, for performance of such operations. In an example embodiment, an apparatus, for example electronic apparatus 10 of FIG. 1, is transformed by having memory, for example memory 12 of FIG. 1, comprising computer code configured to, working with a processor, for example processor 11 of FIG. 1, cause the apparatus to perform set of operations of FIG. 16.

As previously described, it may be desirable to modify an exercise plan to reflect at least one replacement exercise activity.

At block 1602, the apparatus determines an exercise plan for a user of the apparatus, similarly as described regarding block 1102 of FIG. 11. At block 1604, the apparatus enters a collaborative exercise session with a separate apparatus, similarly as described regarding block 1104 of FIG. 11. At block 1606, the apparatus determines a portion of the exercise plan that corresponds with a location of the user, similarly as described regarding block 1106 of FIG. 11. At block 1608, the apparatus causes display of an exercise indicator that indicates exercise instruction information that corresponds with the portion of the exercise plan, similarly as described regarding block 1108 of FIG. 11. At block 1610, the apparatus receives exercise information from the separate apparatus, similarly as described regarding block 1110 of FIG. 11.

At block 1612, the apparatus modifies the exercise plan to generate a modified exercise plan. In this manner, the modification of the exercise plan may be based, at least in part, on the exercise information received from the separate apparatus. The modification of the exercise plan comprises modification of exercise instruction information that is indicative of exercise pace such that corresponding exercise instruction information comprised by the modified exercise plan is indicative of at least one replacement exercise activity. In this manner, the modified exercise plan may reflect at least one replacement exercise activity.

At block 1614, the apparatus determines a portion of the modified exercise plan that corresponds with a location of the user, similarly as described regarding block 1114 of FIG. 11. At block 1616, the apparatus causes display of another exercise indicator that indicates exercise instruction information that corresponds with the portion of the modified exercise plan, similarly as described regarding block 1116 of FIG. 11.

Figure 17:
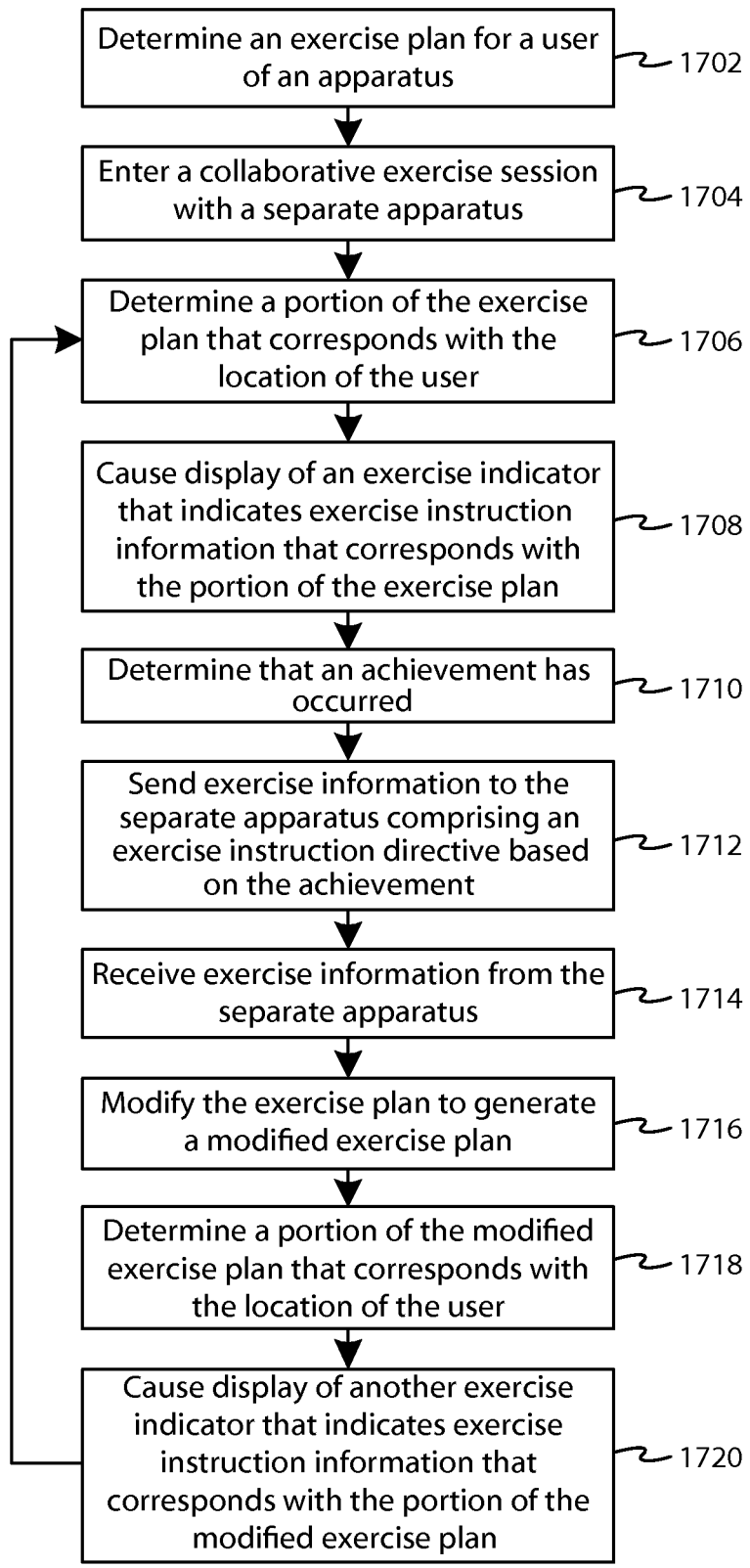
FIG. 17 is a flow diagram illustrating activities associated with determining that an achievement has occurred according to at least one example embodiment.

FIG. 17 is a flow diagram illustrating activities associated with determining that an achievement according to at least one example embodiment. In at least one example embodiment, there is a set of operations that corresponds with the activities of FIG. 17. An apparatus, for example electronic apparatus 10 of FIG. 1, or a portion thereof, may utilize the set of operations. The apparatus may comprise means, including, for example processor 11 of FIG. 1, for performance of such operations. In an example embodiment, an apparatus, for example electronic apparatus 10 of FIG. 1, is transformed by having memory, for example memory 12 of FIG. 1, comprising computer code configured to, working with a processor, for example processor 11 of FIG. 1, cause the apparatus to perform set of operations of FIG. 17.

As previously described, it may be desirable to determine that an achievement has occurred.

At block 1702, the apparatus determines an exercise plan for a user of the apparatus, similarly as described regarding block 1102 of FIG. 11. At block 1704, the apparatus enters a collaborative exercise session with a separate apparatus, similarly as described regarding block 1104 of FIG. 11. At block 1706, the apparatus determines a portion of the exercise plan that corresponds with a location of the user, similarly as described regarding block 1106 of FIG. 11. At block 1708, the apparatus causes display of an exercise indicator that indicates exercise instruction information that corresponds with the portion of the exercise plan, similarly as described regarding block 1108 of FIG. 11.

At block 1710, the apparatus determines that an achievement has occurred. The determination and the achievement may be similar as described regarding FIGS. 10A-10B.

At block 1712, the apparatus sends exercise information to the separate apparatus. The exercise information comprises an exercise instruction directive. In this manner, the exercise instruction directive may be based, at least in part, on the achievement. The sending, the exercise information, and the exercise instruction directive may be similar as described regarding FIGS. 6A-6D, FIG. 8, FIGS. 9A-9C, and FIGS. 10A-10B.

At block 1714, the apparatus receives exercise information from the separate apparatus, similarly as described regarding block 1110 of FIG. 11. At block 1716, the apparatus modifies the exercise plan to generate a modified exercise plan, similarly as described regarding block 1112 of FIG. 11. At block 1718, the apparatus determines a portion of the modified exercise plan that corresponds with a location of the user, similarly as described regarding block 1114 of FIG. 11. At block 1720, the apparatus causes display of another exercise indicator that indicates exercise instruction information that corresponds with the portion of the modified exercise plan, similarly as described regarding block 1116 of FIG. 11.

Figure 18:
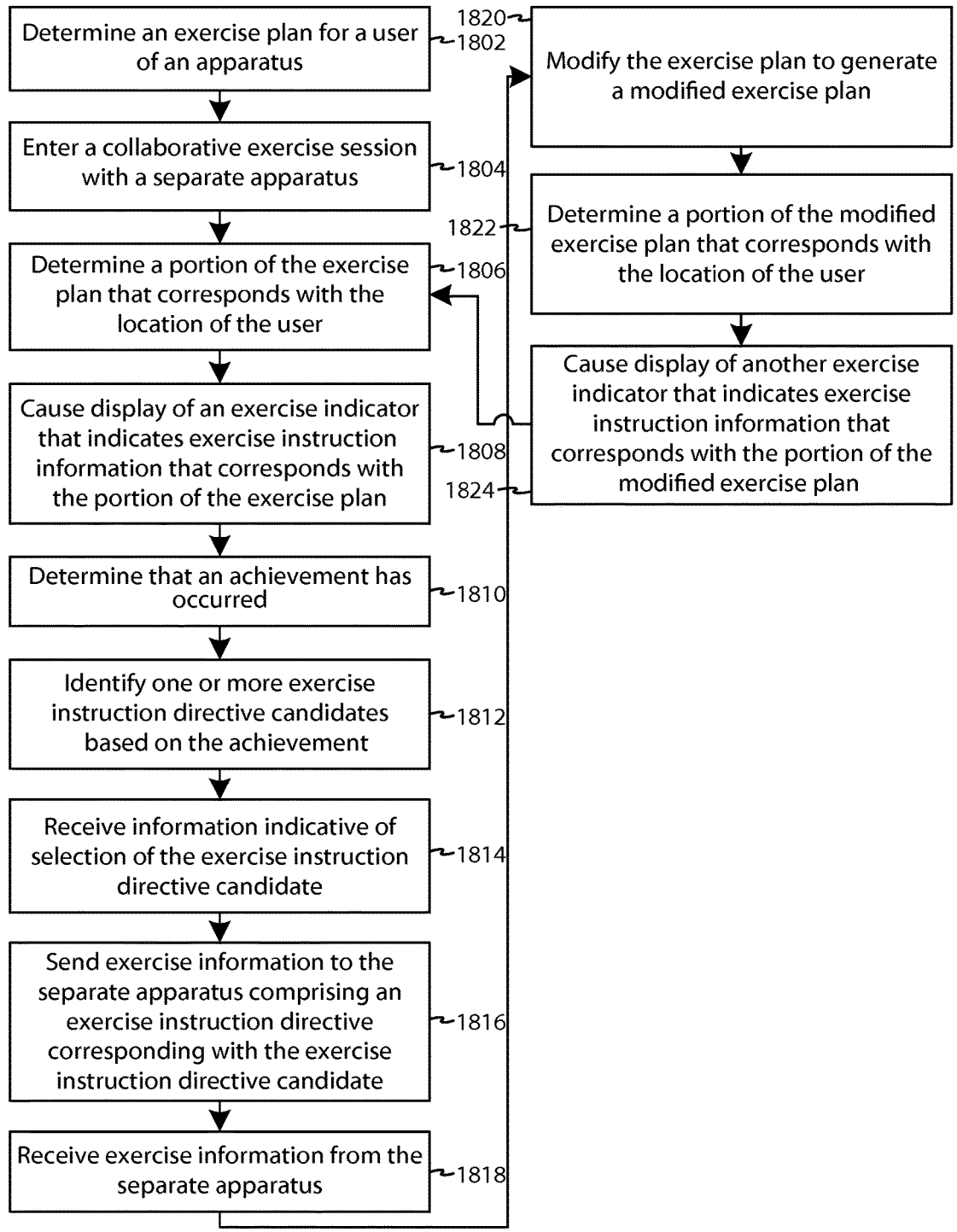
FIG. 18 is a flow diagram illustrating activities associated with sending an exercise instruction directive according to at least one example embodiment.

FIG. 18 is a flow diagram illustrating activities associated with sending an exercise instruction directive according to at least one example embodiment. In at least one example embodiment, there is a set of operations that corresponds with the activities of FIG. 18. An apparatus, for example electronic apparatus 10 of FIG. 1, or a portion thereof, may utilize the set of operations. The apparatus may comprise means, including, for example processor 11 of FIG. 1, for performance of such operations. In an example embodiment, an apparatus, for example electronic apparatus 10 of FIG. 1, is transformed by having memory, for example memory 12 of FIG. 1, comprising computer code configured to, working with a processor, for example processor 11 of FIG. 1, cause the apparatus to perform set of operations of FIG. 18.

As previously described, it may be desirable to send an exercise instruction directive.

At block 1802, the apparatus determines an exercise plan for a user of the apparatus, similarly as described regarding block 1102 of FIG. 11. At block 1804, the apparatus enters a collaborative exercise session with a separate apparatus, similarly as described regarding block 1104 of FIG. 11. At block 1806, the apparatus determines a portion of the exercise plan that corresponds with a location of the user, similarly as described regarding block 1106 of FIG. 11. At block 1808, the apparatus causes display of an exercise indicator that indicates exercise instruction information that corresponds with the portion of the exercise plan, similarly as described regarding block 1108 of FIG. 11. At block 1810, the apparatus determines that an achievement has occurred, similarly as described regarding block 1710 of FIG. 17.

At block 1812, the apparatus identifies one or more exercise instruction directive candidates. In this manner, the identification of the one or more exercise instruction candidates may be based, at least in part, on the achievement. The identification and the exercise instruction candidates may be similar as described regarding FIGS. 10A-10B.

At block 1814, the apparatus receives information indicative of selection of the exercise instruction directive candidate. The receipt and the selection may be similar as described regarding FIGS. 10A-10B.

At block 1816, the apparatus sends exercise information to the separate apparatus. The exercise information comprises an exercise instruction directive corresponding with the exercise instruction directive candidate. In this manner, the exercise instruction directive may be based, at least in part, on the achievement. The sending, the exercise information, and the exercise instruction directive may be similar as described regarding FIGS. 6A-6D, FIG. 8, FIGS. 9A-9C, and FIGS. 10A-10B.

At block 1818, the apparatus receives exercise information from the separate apparatus, similarly as described regarding block 1110 of FIG. 11. At block 1820, the apparatus modifies the exercise plan to generate a modified exercise plan, similarly as described regarding block 1112 of FIG. 11. At block 1822, the apparatus determines a portion of the modified exercise plan that corresponds with a location of the user, similarly as described regarding block 1114 of FIG. 11. At block 1824, the apparatus causes display of another exercise indicator that indicates exercise instruction information that corresponds with the portion of the modified exercise plan, similarly as described regarding block 1116 of FIG. 11.

Embodiments of the invention may be implemented in software, hardware, application logic or a combination of software, hardware, and application logic. The software, application logic, and/or hardware may reside on the apparatus, a separate device, or a plurality of separate devices. If desired, part of the software, application logic, and/or hardware may reside on the apparatus, part of the software, application logic and/or hardware may reside on a separate device, and part of the software, application logic, and/or hardware may reside on a plurality of separate devices. In an example embodiment, the application logic, software or an instruction set is maintained on any one of various conventional computer-readable media.

If desired, the different functions discussed herein may be performed in a different order and/or concurrently with each other. For example, block 1108 of FIG. 11 may be performed after block 1110 of FIG. 11. Furthermore, if desired, one or more of the above-described functions may be optional or may be combined. For example, block 1108 of FIG. 11 may be optional and/or combined with block 1110 of FIG. 11.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the above describes example embodiments of the invention, these descriptions should not be viewed in a limiting sense. Rather, there are variations and modifications which may be made without departing from the scope of the present invention as defined in the appended claims.

The invention claimed is:

1. A method comprising:
   determining, using an apparatus worn by or held by a first user and comprising a processor, a memory, at least one location sensor, at least one orientation sensor, and at least one projector, a location of the apparatus based at least in part on location sensor information, an orientation of the apparatus based at least in part on orientation sensor information, and displaying, from the at least one projector and based on information from the processor, of a field of view of the first user based on the location sensor information and the orientation sensor information;
   determining an exercise plan to be performed by the first user;
   determining a portion of the exercise plan that corresponds with a location of the first user;
   causing display of an exercise indicator, on the field of view, that indicates exercise instruction information that corresponds with the portion of the exercise plan;
   receiving, while the first user is performing the exercise plan, exercise information from a separate apparatus based, at least in part, on a collaborative exercise session, wherein the exercise information corresponds to a second user of the separate apparatus;
   modifying the exercise plan to generate a modified exercise plan based, at least in part, on the exercise information received from the separate apparatus;
   determining a portion of the modified exercise plan that corresponds with the location of the first user; and
   causing display, on the field of view, of another exercise indicator that indicates exercise instruction information that corresponds with the portion of the modified exercise plan; and
   determining the portion of the exercise plan that corresponds with the field of view of the first user;
   wherein the field of view of the first user corresponds with an area on a surface on which information is projected based, at least in part, on the location of the apparatus and the orientation of the apparatus, wherein the area on the surface on which the information is projected corresponds to a physical region in which the information is displayed in the field of view of the first user.

2. The method of claim 1, wherein causing display of the exercise indicator is performed such that the exercise indicator is perceivable by the first user within the area on the surface on which the information is projected.

3. The method of claim 1, wherein the projector is a near eye display and the area on the surface on which the information is projected is a physical region that is viewable through the near eye display.

4. The method of claim 1, wherein modifying the exercise plan is performed such that the modified exercise plan reflects a changed exercise pace from the exercise plan.

5. The method of claim 1, wherein modifying the exercise plan comprises modification of exercise instruction information that is indicative of exercise pace such that corresponding exercise instruction information comprised by the modified exercise plan is indicative of at least one additional exercise activity.

6. The method of claim 1, wherein modifying the exercise plan comprises modification of exercise instruction information that is indicative of exercise pace such that corresponding exercise instruction information comprised by the modified exercise plan is indicative of at least one replacement exercise activity.

7. The method of claim 1, further comprising sending exercise information comprising an exercise instruction directive to the separate apparatus.

8. The method of claim 7, further comprising:
    determining that an achievement has occurred, wherein the exercise instruction directive is based, at least in part, on the achievement;
    identifying one or more exercise instruction directive candidates based, at least in part, on the achievement; and
    receiving information indicative of selection of the exercise instruction directive candidate, wherein the exercise instruction directive corresponds with the exercise instruction directive candidate.

9. An apparatus comprising a processor and a memory including computer program code, the memory and the computer program code configured to, with the processor, cause the apparatus to:
    determine, using the apparatus worn by or held by a first user and comprising the processor and the memory and further comprising at least one location sensor, at least one orientation sensor, and at least one projector, a location of the apparatus based at least in part on location sensor information, an orientation of the apparatus based at least in part on orientation sensor information, and displaying, from the at least one projector and based on information from the processor, of a field of view of the first user based on the location sensor information and the orientation sensor information;
    determine an exercise plan to be performed by the first user;
    determine a portion of the exercise plan that corresponds with a location of the first user;
    cause display of an exercise indicator, on the field of view, that indicates exercise instruction information that corresponds with the portion of the exercise plan;
    receive, while the first user is performing the exercise plan, exercise information from a separate apparatus based, at least in part, on a collaborative exercise session, wherein the exercise information corresponds to a second user of the separate apparatus;
    modify the exercise plan to generate a modified exercise plan based, at least in part, on the exercise information received from the separate apparatus;
    determine a portion of the modified exercise plan that corresponds with the location of the first user; and
    cause display, on the field of view, of another exercise indicator that indicates exercise instruction information that corresponds with the portion of the modified exercise plan; and
    determine the portion of the exercise plan that corresponds with the field of view of the first user;
    wherein the field of view of the first user corresponds with an area on a surface on which information is projected based, at least in part, on the location of the apparatus and the orientation of the apparatus, wherein the area on the surface on which the information is projected corresponds to a physical region in which the information is displayed in the field of view of the first user.

10. The apparatus of claim 9, wherein the memory and the computer program code are further configured to, with the processor, cause the apparatus to display the exercise indicator such that the exercise indicator is perceivable by the first user within the area on the surface on which the information is projected.

11. The apparatus of claim 9, wherein the projector is a near eye display and the area on the surface on which the information is projected is a physical region that is viewable through the near eye display.

12. The apparatus of claim 9, wherein the memory and the computer program code are further configured to, with the processor, cause the apparatus to modify the exercise plan such that the modified exercise plan reflects a changed exercise pace from the exercise plan.

13. The apparatus of claim 9, wherein the memory and the computer program code are further configured to, with the processor, cause the apparatus to modify the exercise plan so that modification of exercise instruction information that is indicative of exercise pace such that corresponding exercise instruction information comprised by the modified exercise plan is indicative of at least one additional exercise activity.

14. The apparatus of claim 9, wherein the memory and the computer program code are further configured to, with the processor, cause the apparatus to send exercise information comprising an exercise instruction directive to the separate apparatus.

15. The apparatus of claim 14, wherein the memory and the computer program code are further configured to, with the processor, cause the apparatus to
    determine that an achievement has occurred, wherein the exercise instruction directive is based, at least in part, on the achievement;
    identify one or more exercise instruction directive candidates based, at least in part, on the achievement; and
    receive information indicative of selection of the exercise instruction directive candidate, wherein the exercise instruction directive corresponds with the exercise instruction directive candidate.

16. Computer program product comprising a non-transitory computer readable medium having program code portions stored thereon, the program code portions being a computer readable medium and configured when said program product is run on a computer or network device, to:
    determine, using an apparatus worn by or held by a first user and comprising a processor, a memory, at least one location sensor, at least one orientation sensor, and at least one projector, a location of the apparatus based at least in part on location sensor information, an orientation of the apparatus based at least in part on orientation sensor information, and displaying, from the at least one projector and based on information from the processor, of a field of view of the first user based on the location sensor information and the orientation sensor information;
    determine an exercise plan to be performed by the first user;
    determine a portion of the exercise plan that corresponds with a location of the first user;

cause display of an exercise indicator, on the field of view, that indicates exercise instruction information that corresponds with the portion of the exercise plan;

receive, while the first user is performing the exercise plan, exercise information from a separate apparatus based, at least in part, on a collaborative exercise session, wherein the exercise information corresponds to a second user of the separate apparatus;

modify the exercise plan to generate a modified exercise plan based, at least in part, on the exercise information received from the separate apparatus;

determine a portion of the modified exercise plan that corresponds with the location of the first user; and cause display, on the field of view, of another exercise indicator that indicates exercise instruction information that corresponds with the portion of the modified exercise plan; and determine the portion of the exercise plan that corresponds with the field of view of the first user;

wherein the field of view of the first user corresponds with an area on a surface on which information is projected based, at least in part, on the location of the apparatus and the orientation of the apparatus, wherein the area on the surface on which the information is projected corresponds to a physical region in which the information is displayed in the field of view of the first user.

* * * * *